US010828265B2

(12) United States Patent
Aoyagi et al.

(10) Patent No.: US 10,828,265 B2
(45) Date of Patent: Nov. 10, 2020

(54) FORMULATIONS OF PROPRANOLOL AND ANALOGS AS AN AMORPHOUS MELT OR IONIC LIQUID FOR TRANSDERMAL DRUG DELIVERY

(71) Applicant: The Regents of the University of California, Oakland, CA (US)

(72) Inventors: Kazuhiro Aoyagi, Miyagi (JP); Michael Zakrewsky, San Diego, CA (US); Samir Mitragotri, Lexington, MA (US)

(73) Assignee: The Regents of the University of California, Oakland, CA (US)

(*) Notice: Subject to any disclaimer, the term of this patent is extended or adjusted under 35 U.S.C. 154(b) by 234 days.

(21) Appl. No.: 15/837,420

(22) Filed: Dec. 11, 2017

(65) Prior Publication Data
US 2018/0169033 A1 Jun. 21, 2018

Related U.S. Application Data

(60) Provisional application No. 62/432,405, filed on Dec. 9, 2016.

(51) Int. Cl.
*A61K 9/70* (2006.01)
*A61K 9/00* (2006.01)
(Continued)

(52) U.S. Cl.
CPC .......... *A61K 9/7038* (2013.01); *A61K 9/0014* (2013.01); *A61K 9/0095* (2013.01);
(Continued)

(58) Field of Classification Search
None
See application file for complete search history.

(56) References Cited

U.S. PATENT DOCUMENTS 4,042,327 A * 8/1977 Haney ............... G01N 30/48
436/161
4,892,737 A 1/1990 Bodor
(Continued)

FOREIGN PATENT DOCUMENTS

CN 105434337 A * 3/2016
JP 2008184407 4/2008
(Continued)

OTHER PUBLICATIONS

Aoyagi et al. "Formulating propranolol as an amorphous melt affords reduced skin irritation potential for transdermal drug delivery" Technology, vol. 3, No. 4, Dec. 2015, pp. 214-238. (Year: 2015).*

(Continued)

*Primary Examiner* — Carlos A Azpuru
*Assistant Examiner* — Casey S Hagopian
(74) *Attorney, Agent, or Firm* — Pabst Patent Group LLP

(57) ABSTRACT

Melts or ionic liquids containing amorphous propranolol, topical formulations and patches for transdermal drug delivery, and methods of making and using thereof are described herein. The melts or ionic liquids may be in a topical drug delivery formulation or patch to be applied to the skin. The drug delivery formulation or patch contains a sufficient amount of the amorphous propranolol to deliver a therapeutically effective amount of the amorphous propranolol to the patient in need of treatment, such as for the treatment or amelioration of infantile hemangioma. The formulations have a low viscosity and reduced skin irritation compared to the crystalline propranolol free base (PFB). The melts or ionic liquids can be formed by a salt metathesis reaction.

28 Claims, 14 Drawing Sheets

(51) Int. Cl.
| | |
|---|---|
| A61K 31/138 | (2006.01) |
| A61K 31/194 | (2006.01) |
| A61P 35/00 | (2006.01) |
| A61K 47/12 | (2006.01) |
| A61K 47/32 | (2006.01) |
| A61K 47/38 | (2006.01) |
| A61K 47/10 | (2017.01) |
| A61K 47/20 | (2006.01) |

(52) U.S. Cl.
CPC .......... *A61K 31/138* (2013.01); *A61K 31/194* (2013.01); *A61K 47/10* (2013.01); *A61K 47/12* (2013.01); *A61K 47/20* (2013.01); *A61K 47/32* (2013.01); *A61K 47/38* (2013.01); *A61P 35/00* (2018.01)

(56) References Cited

U.S. PATENT DOCUMENTS

| | | | |
|---|---|---|---|
| 5,965,610 | A | 10/1999 | Modak |
| 6,858,217 | B2 | 2/2005 | Kerschner |
| 7,102,000 | B2 | 9/2006 | Pfahl |
| 2006/0110434 | A1* | 5/2006 | Yamaguchi .......... A61K 9/7053 424/448 |
| 2010/0256174 | A1 | 10/2010 | Yamaguchi |
| 2014/0322307 | A1 | 10/2014 | Ferrer Montiel |
| 2015/0342852 | A1 | 12/2015 | Van Den Nest |
| 2016/0263225 | A1 | 9/2016 | Zakrewsky |

FOREIGN PATENT DOCUMENTS

| | | |
|---|---|---|
| JP | 2008184402 | 8/2008 |
| WO | 2003055455 | 7/2003 |
| WO | 2007124397 | 11/2007 |
| WO | 2008031105 | 3/2008 |
| WO | 2009066457 | 5/2009 |
| WO | 2011056545 | 5/2011 |
| WO | 2015066647 | 5/2015 |

OTHER PUBLICATIONS

"Propranolol" accessed online on Feb. 1, 2020 at https://pubchem.ncbi.nlm.nih.gov/compound/Propranolol. (Year: 2020).*
Abbott et al., "Eutectic-Based Ionic Liquids with Metal-Containng Anions and Cations"—Chemistry, A European Journal, 13, 6495-6501, Jul. 27, 2007.
Abbott, et al., "Design of improved deep eutectic solvents using hole theory" ChemPhysChem, 7(4): p. 803-806 (2006).
Abbott, et al., "Novel solvent properties of choline chloride/urea mixtures" Chem. Commun. (Camb), (1): 70-71 (2003).
Am. Chem., "Efficacy of ionic liquids for pathogen neutralization: Turntable solvents as anti-biofilm agents," Abstracts, 39th Northeast Regional meeting of the American Chemical Society, New Haven, Ct., Oct. 23-26, 1 page, (Oct. 25, 2013).
Amnuaikit et al., "Skin permeation of propranolol from polymeric film containing terpene enhancers for transdermal use," Int. J. Pharm., 289:167-78 (2005).
Baker, et al., "Fluorescence studies of protein thermostability in ionic liquids" Chemical Commun (Camb), (8): 940-1 (2004).
Brown, et al., "Dermal and transdermal drug delivery systems: current and future prospects" Drug Delivery, 13:175-87 (2006).
Carson, et al., "Antibiofilm activities of 1-alkyl-3-methylimidazolium chloride ionic liquids" Green Chem., 11(4):492-7 (2009).
Cojocaru, et al., "Prodrug ionic liquids: Functionalizing neutral active pharmaceutical ingredients to take advantage of the ionic liquid form," Med Chem Comm., 4:559-63 (2013).
Del Sesto, et al., "Tetraalkylphosphonium-based ionic liquids," J Organometallic Chem., 690(10): 2536-42 (2004).
Dobler, et al., "Ionic liquids as ingredients in topical drug delivery," Int J Pharma, 441((1-2):620-7 (2013).
Hayyan, et al., "Glucose-based deep eutectic solvents: Physical properties," J Mol Liq., 178: 137-41 (2013).
Hori et al.,"Enhancement of propranolol hydrochloride and diazepam skin absorption in vitro: Effect of enhancer lipophilicity," J. Pharm. Sci., 80:32-35 (1991).
Hough, et al., "The third evolution of ionic liquids: Active pharmaceutical ingredients," N. J. Chem., 31:1429 (2007).
International Search Report for PCT/US2014/063745 dated Apr. 28, 2015.
Karande, et al., "Design principles of chemical penetration enhancers for transdermal drug delivery," PNAS, 102:4688-93 (2005).
Karande, et al., "Discovery of transdermal penetration enhancers by high-throughput screening," Nat Biotechnol, 22(2):192-7 (2004).
Kobayashi, et al., "Skin toxicity of propranolol in guinea pigs," J. Toxicol. Sci., 24:103-12 (1999).
Krishna and Pandit,"Transdermal delivery of propranolol" Drug Dev. Ind. Pharm., 20:2459-65 (1994).
Lovejoy, et al., "Utilization of Metal Halide Species Ambiguity to Develop Amorphous, Stabilized Pharmaceutical Agents as Ionic Liquids" Crystal Growth & Design, 12(11): p. 5357-64 (2012).
Macfarlane, et al., "Pyrrolidinium imides: A new family of molten salts and conductive plastic crystal phases," J Phys Chem., 103(20):4164-70 (1999).
Martin, et al., "Impact of physicochemical properties of engineered fullerenes on key biological responses," Toxicol Appl Pharmacol., 234(1):58-67 (2009).
Palmer, et al., "Molecular techniques to detect biofilm bacteria in long bone nonunion: a case report," Clin orthop relat Res., 469:3037-42 (2011).
Partial European Search Report dated May 29, 2017 in European Patent Application No. 14859243.9.
Pine, et al., "Correlation of plasma propranolol concentration with therapeutic response in patients with angina pectoris," Circulation, 52:886-93 (1975).
Thacharodi and Rao, "Development and in vitro evaluation of chitosan-based transdermal drug delivery systems for the controlled delivery of propranolol hydrochloride" Biomaterials, 16: 145-8 (1995).
Wilkes, et al., "Dialkylimidazolium Chloroaluminate Melts—a New Class of Room-Temperature Ionic Liquids for Electrochemistry, Spectroscopy and Synthesis" Inorg Chem., 21(3):1263-64 (1982).
Yu, et al., "Biodegradable naphthenic acid ionic liquids: synthesis, characterization, and quantitative structure-biodegradation relationship," Chem., 14(35):11174-82 (2008).
Zakrewsky, et al., "Ionic liquids as a class of materials for transdermal delivery and pathogen neutralization," PNAS, 111:13313-8 (2014).

* cited by examiner

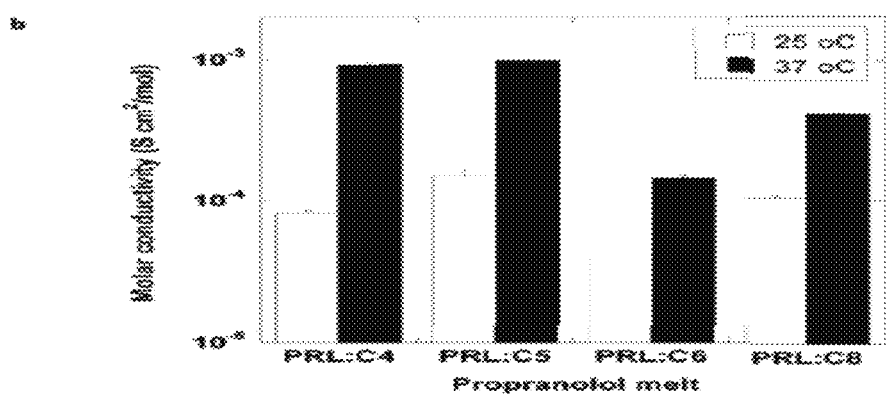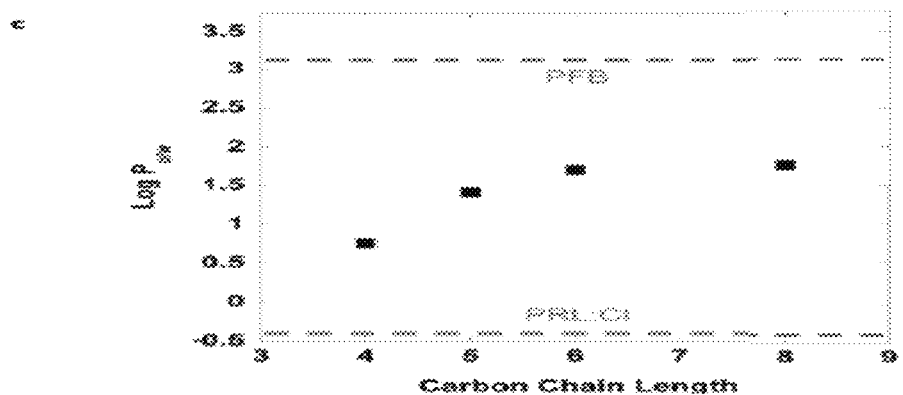
Figures 6A – 6C

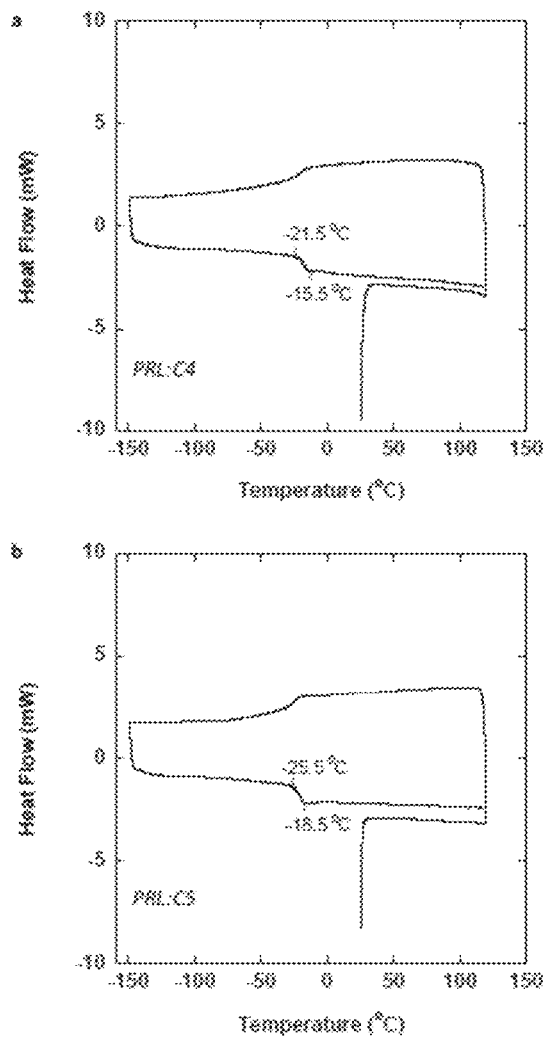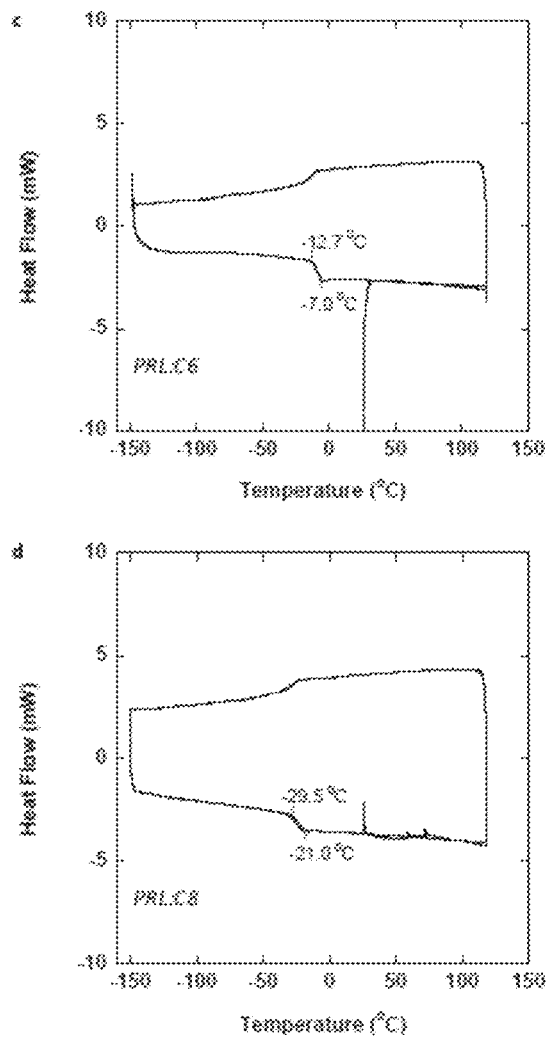
Figures 12A – 12D

FORMULATIONS OF PROPRANOLOL AND ANALOGS AS AN AMORPHOUS MELT OR IONIC LIQUID FOR TRANSDERMAL DRUG DELIVERY

CROSS-REFERENCE TO RELATED APPLICATION

This application claims benefit of and priority to U.S. Ser. No. 62/432,405, filed Dec. 19, 2016, the disclosure of which is herein incorporated by reference in their entirety.

FIELD OF INVENTION

The field of the invention is formulations for transdermal drug delivery, more specifically formulations of propranolol as an amorphous melt or ionic liquid to afford reduced potential for skin irritation.

Propranolol melt or ionic liquids may be applicable for the topical treatment of infantile hemangioma.

BACKGROUND

Infantile hemangioma (IH) is the most common form of infantile tumor and if untreated can result in significant physical disfigurement due to ulceration and scarring of skin lesions. Bruckner, A. L. & Frieden, U., "Hemangiomas of infancy", *J. Am. Acad. Dermatol*, 48: 477-93 (2003). Despite its prevalence and the severity of complications, there is no Food and Drug Administration (FDA)-approved therapeutic for IH leaving, clinicians with few robust treatment options. Drolet, et al., "*Initiation and use of propranolol for infantile hemangioma: Report of a consensus conference*", Pediatrics, 131: 128-40 (2013).

Oral propranolol has garnered considerable off-label use to fill this void, but not without significant drawbacks. Limitations of oral delivery of propranolol include significant first-pass metabolism, poor accumulation in skin lesions and consequently, systemic side effects, such as sleep disturbances, diarrhea, gastric reflux, and hypoglycemia. Holmes, W. J., et al., "Propranolol as first-line treatment for rapidly proliferating infantile hemangiomas", *J. Plast. Reconstr. Aesthet. Surg*, 64: 445-51 (2011) and Drolet, B. A. et al., "Initiation and use of propranolol for infantile hemangioma: Report of a consensus conference", *Pediatrics* 131, 128-140 (2013).

The topical application of propranolol may offer significant advantages over oral delivery including targeted delivery to the site of skin lesions while concurrently minimizing systemic saturation and the negative side effects resulting thereof. Prausnitz, M. R., Mitragotri, S. & Langer, R., "Current status and future potential of transdermal drug delivery", *Nat. Rev. Drug Discov.* 3, 115-124 (2004). Further, topical application affords direct observation of the application site. This is particularly advantageous for the treatment of IH for which there is no consensus among administrators on the appropriate dosing, schedule and duration of propranolol treatment.

Topical delivery, however, presents its own challenges. The delivery through the skin is limited by certain disadvantages, including the restriction on drug size, requirement of adequate aqueous, and lipid solubility and issues of skin irritation and sensitization. Brown, M. B., et al., Dermal and transdermal drug delivery systems: Current and future prospects. *Drug Deliv.* 13, 175-187 (2006).

In particular, skin irritation caused by the chemical stimulus of drugs, excipients and solvents often poses a significant challenge in the design of dermal and transdermal formulations. For example, propranolol has been evaluated extensively in transdermal formulations, and several different formulations have demonstrated therapeutically viable doses delivered (Hori, M., et al., Enhancement of propranolol hydrochloride and diazepam skin absorption in vitro: Effect of enhancer lipophilicity. *J. Pharm. Sci.* 80, 32-35 (1991); Thacharodi, D. & Rao, K. Development and in vitro evaluation of chitosan-based transdermal drug delivery systems for the controlled delivery of propranolol hydrochloride. *Biomaterials* 16, 145-148 (1995); Amnuaikit, C., et al., Skin permeation of propranolol from polymeric film containing terpene enhancers for transdermal use. *Int. J. Pharm.* 289, 167-178 (2005)); however, dose-dependent skin inflammatory responses have significantly limited their use. Krishna, R. & Pandit, J., Transdermal delivery of propranolol. *Drug Dev. Ind. Pharm.* 20, 2459-2465 (1994); Kobayashi, I. et al., Skin toxicity of propranolol in guinea pigs. *J. Toxicol. Sci.* 24, 103-112 (1999).

Local skin irritation still represents an unmet issue and additional strategies to mitigate irritation are necessary. Remarkable ability of Ionic Liquids (IL) and deep eutectic formulations to reduce or eliminate the irritation potential of their respective components, i.e., two chemicals that are irritating to skin when applied alone become non-irritating when combined together as an amorphous melt or ionic liquid. Zakrewsky, M. et al. Ionic liquids as a class of materials for transdermal delivery and pathogen neutralization. *Proc. Natl. Acad. Sci. USA* 111, 13313-13318 (2014).

SUMMARY OF THE INVENTION

Amorphous melts of propranolol with sufficiently low viscosity such that they can be applied directly on the skin without the need for the addition of an organic solvent, and formulations and compositions containing such melts and ionic liquids are described herein. The formulation or patch containing the formulation may be applied at the site in need of treatment, such as the site of a skin lesion.

Formulations suitable for topical application to the skin containing therapeutic doses of propranolol for the treatment of skin diseases, such as IH, are described herein. The formulations often have improved transdermal transport compared to propranolol free base (PFB) in solution. Typically, when the formulations are applied to the skin, the skin has less irritation to the formulations compared to PFB in solution.

Methods for making compositions containing propranolol with improved transdermal transport compared to PFB are also described.

Method for making compositions containing propranolol with reduced potential for skin irritation compared to PFB are also described.

Methods for treating skin diseases, such as IH, by the topical administration of the formulations described herein. Optionally, the formulations are provided in or applied to a topical delivery device, such as a patch, and then applied to the skin.

The compositions and methods of preparing a propranolol amorphous melt or ionic liquid described herein are applied topically to the skin with reduced skin irritation compared to the crystalline propranolol free base (PFB) in solution. The compositions have a sufficiently low viscosity (59.5~1,889.4 Pa·S), such that they can be directly applied to the skin without need of organic solvent. The melt or ionic liquid possesses identical delivery efficiency to PFB, but affords a significantly high flux (0.01 mg/cm$^2$ to 10 mg/cm$^2$) due to inherent solubility limitation of crystalline salt and free base in an aqueous and organic solvent.

The melt or ionic liquid showed reduced skin irritation potential compared to the free base in solution. Four analog propranolol melts or ionic liquids were synthesized by salt metathesis of propranolol hydrochloride (PRL:Cl) and sodium dialkyl sulfosuccinates.

In a preferred embodiment, propranolol formulations reduce skin irritation without compromising skin transport efficiency. These formulations are applied topically to the surface of the skin and increase transdermal transport of the drug with less skin irritation compared to the free base in solution.

In some embodiments, amorphous melts or ionic liquids of propranolol have a sufficiently low viscosity such that they can be applied directly on the skin without the need for addition of organic solvent.

In other embodiments, the melts or ionic liquids possess identical delivery efficiency to PFB, but afford a significantly higher flux due to inherent solubility limitations of crystalline salt and free base in an aqueous and organic solvent.

In other embodiments, amorphous melts or ionic liquids of propranolol can be administered to a patient for the treatment of infantile hemangiomas. The melts or ionic liquids of PRL:C8 demonstrate excellent delivery potential and low viscosities, thus offering ease of handling.

As shown by the Examples, the melts possessed identical delivery efficiency to PFB, but afforded a significantly higher flux due to inherent solubility limitations of crystalline salt and free base in an aqueous and organic solvent. Moreover, the lead melt showed reduced skin irritation potential compared to the free base in solution.

The above-mentioned summary presents a simplified version of one or more embodiments in order to provide a basic understanding of the embodiments. The summary is not an extensive overview of all contemplated embodiments, and is intended to neither identify key or critical elements of all embodiments nor delineate the scope of any or all embodiments. Its sole purpose is to present illustrative examples of one or more embodiments. Other aspects will be apparent from the following description, figures and the appended claims.

BRIEF DESCRIPTION OF THE DRAWINGS

FIGS. 6A-6C are panels of propranolol melts or ionic liquids tested for transport across porcine skin and skin irritation. Propranolol melts or ionic liquids were prepared from propranolol hydrochloride and sodium dialkyl sulfosuccinates, and physicochemical properties were characterized. FIG. 6A is a table listing the molecular weight, density and molarity of various melts or ionic liquids which were tested. FIG. 6B is a bar chart of molar conductivity of neat melts or ionic liquids at 25° C. (open bars) and 37° C. (closed bars). Error bars represent mean+SD for n=3. FIG. 6C is a graph of the partition coefficient n-octanol/water (log $P_{o/w}$) values of melts or ionic liquids plotted versus carbon chain length of dialkyl sulfosuccinate. Error bars represent mean±SD for n=3. Log $P_{o/w}$ of propranolol hydrochloride (PRL:Cl) and crystalline propranolol free base (PFB) are shown as dashed lines.

FIG. 7A is a bar chart showing propranolol penetration into individual layers in the porcine skin using various formulations. Delivery depth increases from left to right: 0.1 M PFB in EtOH (open bars), 0.2 M PFB in EtOH (hatched bars), 0.04 M PFB in isopropyl myristate (IPM) (lateral-striped bars) and 0.04 M PRL:C8 in IPM (gray closed bars), neat PRL:C8 (black closed bars). FIG. 7B shows propranolol penetration into individual layers in the porcine skin using neat propranolol melts or ionic liquids in four different DSS formulations. Delivery depth increases from left to right: PRL:C4 (open bars), PRL:C5 (hatched bars), PRL:C6 (cross-hatched bars) and PRL:C8 (black closed bars). FIG. 7C presents permeability of the applied formulations corresponding to the graph shown in FIG. 7A. FIG. 7D shows permeability of the applied formulations corresponding to the graph shown in FIG. 7B. Error bars represent mean+SD for n=3. *p<0.05 compared with PRL:C8 by one-way ANOVA and Bonferroni post-hoc test.

FIG. 8A shows interleukin-1α release as an indicator of irritation was divided by dose (0.1 mg to 10 mg) of applied formulation. Two neat propranolol melts or ionic liquids (PRL:C8 and PRL:C5) and 0.1 M and 0.2 M PFB EtOH solutions were applied on the human skin equivalent tissues. Positive control (5% SDS in PBS-5% Sodium dodecyl sulfate in phosphate buffered saline) was also evaluated. FIG. 8B shows interleukin-1α release as an indicator of irritation was divided by delivered dose in acceptor solution in skin transport test. Error bars represent mean+SD for n=3. *p<0.05 compared with 0.1 M PFB ethanol solution by one-way ANOVA and Bonferroni post-hoc test.

(FIG. 9A) and 37° C. (FIG. 9B). Measured conductivities were normalized by molar concentration: sodium chloride (solid square), propranolol hydrochloride (open square), PRL:C5 (solid circle) and PRL:C8 (open circle). Error bars represent mean±SD for n=3.

FIG. 10A is C4, PFB, PRL:Cl, and PRL:C4; while FIG. 10B is C5, PFB, PRL:Cl, and PRL:C5; FIG. 10C is C6, PFB, PRL:Cl, and PRL:C6; and FIG. 10D is C8, PFB, PRL:Cl, and PRL:C8. PRL:Cl and PFB are duplicated in each figure pane for easy comparison. FIG. 10E shows 875-675 cm$^{-1}$ region where amine wagging and twisting peaks of propranolol melts or ionic liquids show a positive shift compared to PFB, which is indicative of salt formation. An identical positive shift is observed for PRL:Cl.

FIG. 11A is C4, PFB, PRL:Cl, and PRL:C4; FIG. 11B is C5, PFB, PRL:Cl, and PRL:C5; and FIG. 11C is C6, PFB, PRL:Cl, and PRL:C6. FIG. 11D is C8, PFB, PRL:Cl and PRL:C8. PRL:Cl and PFB are duplicated in each figure pane for easy comparison. Data is shown as weight percent.

FIGS. 12A-12D show differential scanning calorimetry (DSC) thermograms of propranolol melts or ionic liquids. FIG. 12A is PRL:C4. FIG. 12B is PRL:C5. FIG. 12C is PRL:C6. FIG. 12D is PRL:C8.

FIG. 13A is 0.1 M PFB EtOH formulation (open bars), 0.2 M PFB EtOH formulation (checkered bars), 0.04 M PFB IPM formulation (lateral-striped bars) and 0.04 M PRL:C8 in IPM (gray closed bars), neat PRL:C8 (black closed bars). FIG. 13B is neat PRL:C4 (open bars), neat PRL:C5 (checkered bars), neat PRL:C6 (gray closed bars) and neat PRL:C8 (black closed bars). Error bars represent mean+SD for n=3. *p<0.05 compared with PRL:C8 by one-way ANOVA and Bonferroni post-hoc test.

FIG. 14A is a graph showing interleukin-la release as an indicator of irritation normalized to the positive control (5% SDS in PBS, a known skin irritant). Error bars represent mean+SD for n=3. *p<0.05 compared with PBS by one-way ANVA and Bonferroni post-hoc test. FIG. 14B shows release of interleukin-la as an indicator of irritation was divided by dose of applied formulation. Interleukin-la release due to solvent (PBS or EtOH) was subtracted from that of SDS or PFB formulations before dividing by applied dose. Error bars represent mean+SD for n=3. *p<0.05 compared with 0.1 M PFB EtOH formulation by one-way ANOVA and Bonferroni post-hoc test.

DETAILED DESCRIPTION

Figure 1:
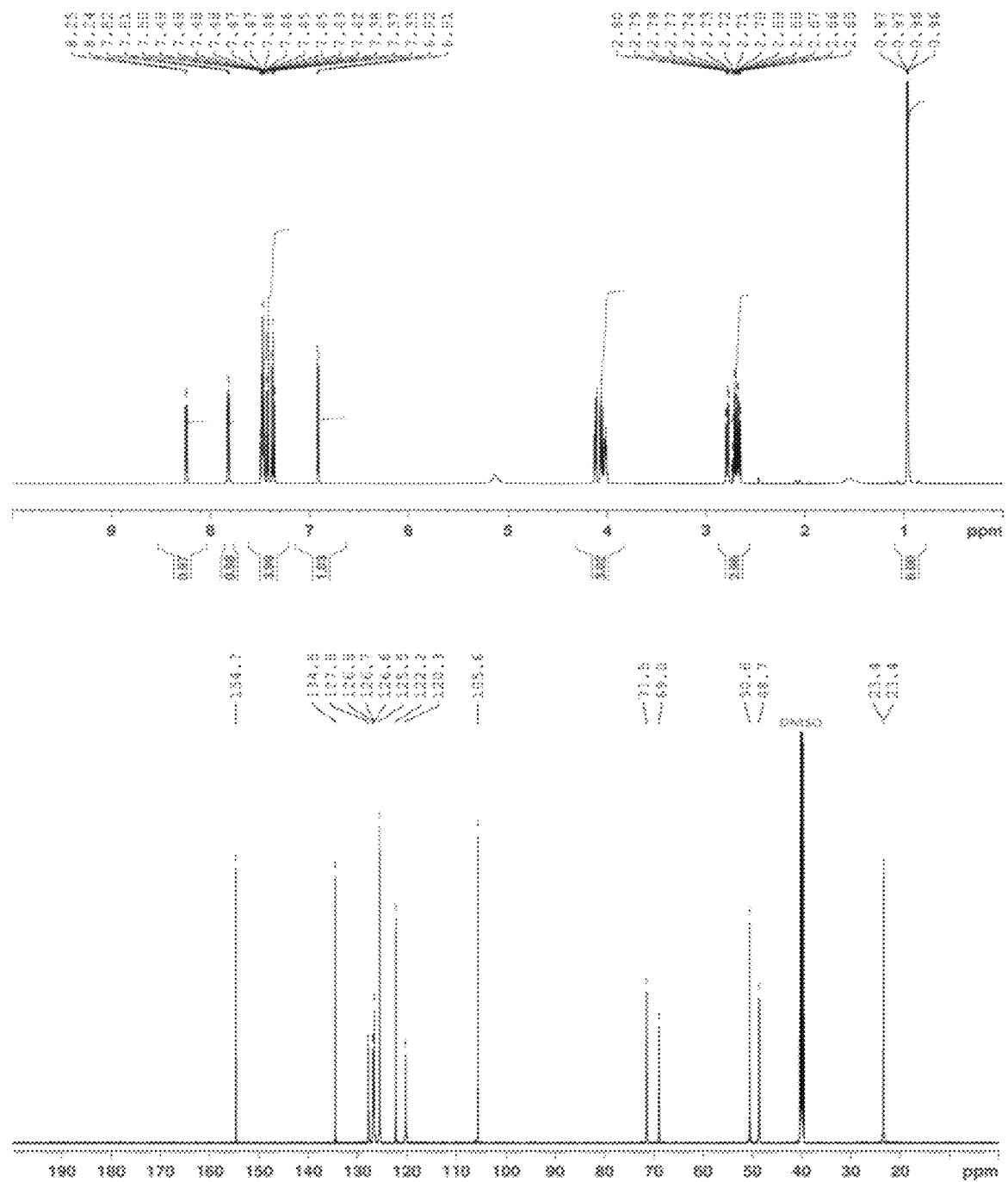
FIG. 1 is an NMR spectra of synthesized PFB powder.

A flow diagram of a step-wise process to formulate propranolol as an amorphous melt or ionic liquid is illustrated in the schematic below (Scheme 1, parts A and B).

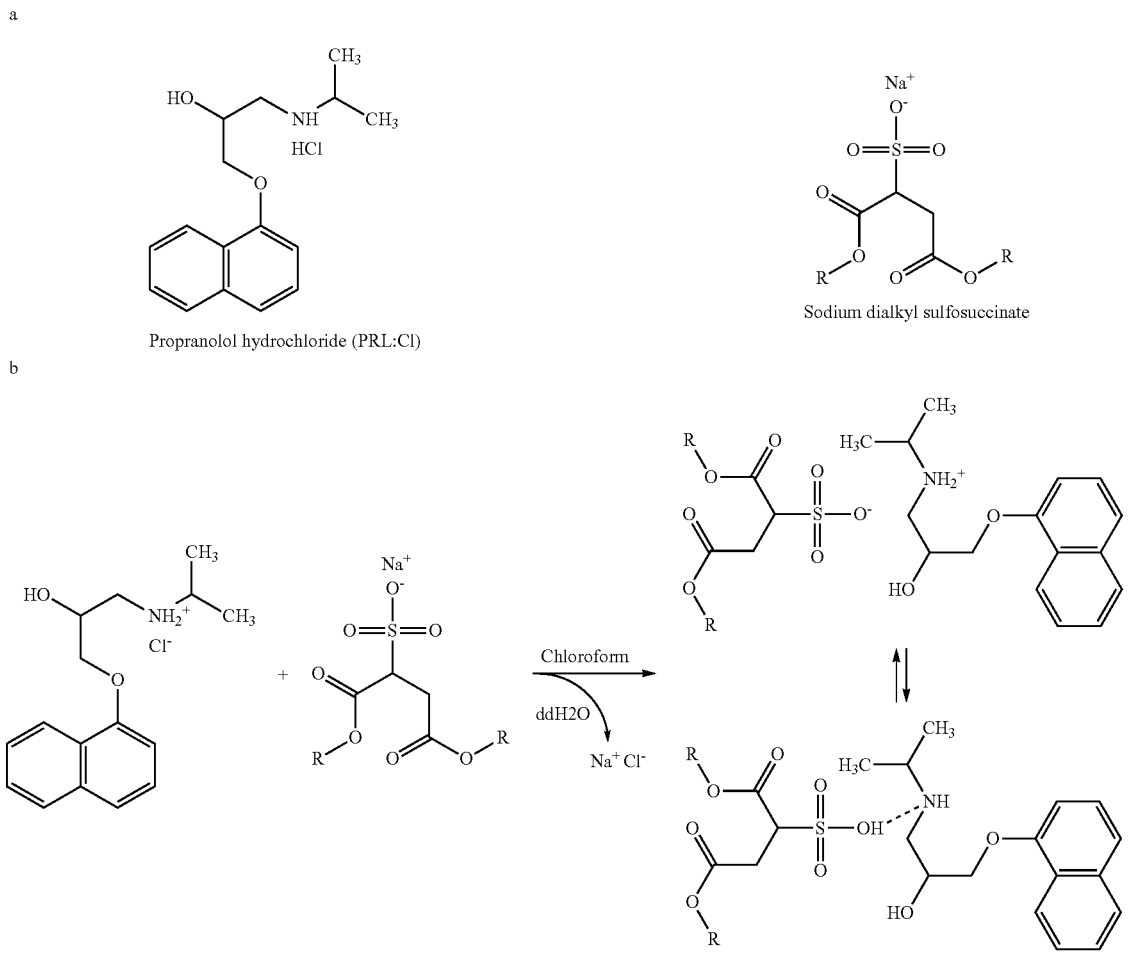

Scheme 1, part a shows the chemical structure of propranolol hydrochloride and sodium dialkyl sulfosuccinate. The alkyl groups (R) of the four sodium dialkyl sulfosuccinates used in the examples were isobutyl (C4), amyl (C5), hexyl (C6) and octyl (C8). They correspond to the following four drug formulations, respectively: propranolol isobutyl sulfosuccinate (PRL:C4), propranolol diamyl sulfosuccinate (PRL:C5), propranolol dihexyl sulfosuccinate (PRL:C6) and propranolol dioctyl sulfosuccinate (PRL:C8). Dialkyl sulfosuccinates are available at low cost and relatively safe compared to other surfactants. Dialkyl sulfosuccinates typically result in melts or ionic liquids with relatively low viscosity, compared to melts or ionic liquids with other counter species. This aids in ease of handling when applying formulations neat on the skin.

Scheme 1, part b shows a simple salt metathesis reaction scheme to synthesize propranolol melts or ionic liquids. Sodium salt and hydrochloride salt were mixed in a 1:1 molar ratio in $ddH_2O$ followed by extraction of organic species in chloroform. The chloroform solution was washed repeatedly with fresh $ddH_2O$ to drive salt metathesis to completion. Complete removal of chloride from the chloroform solution was verified by monitoring the chloride content of the wash solution with Quantofix chloride test strips as well as the silver nitrate precipitation test. The pH of the wash solution was also monitored to ensure washing of the chloroform solution with $ddH_2O$ did not selectively remove hydrochloric acid as opposed to driving salt metathesis. Following complete removal of chloride from the chloroform solution, chloroform was removed by rotary evaporation and the resulting propranolol formulation was dried in a vacuum oven at 60° C. for 36 hours and then stored in a desiccator in the dark until use. All propranolol melts or ionic liquids possessed transparency and fluidity at room temperature. All melts or ionic liquids comprised a water content of roughly 2-3% wt. determined by Karl-Fischer titration. Water content could be reduced to undetectable levels by vacuum drying and repeatedly purging with nitrogen over the course of several weeks. After removal of residual water the melts or ionic liquids retained transparency and fluidity, albeit reduced fluidity, verifying successful synthesis of amorphous melts or ionic liquids and not simply concentrated solutions in water. After exposure to air, however, melts or ionic liquids quickly absorb water and return to 2-3% residual water within a few hours. Melts or ionic liquids retained 2-3% water content unless left open to atmosphere in the dark for more than a week at room temperature, after which they absorb upwards of 10-15% water with a corresponding browning in color. As 2-3% residual water content is inevitably the condition in which propranolol melts or ionic liquids will predominantly interact with the skin when applied neat for 24 hours, this is the condition was used to characterize the melts or ionic liquids and performed all experiments. Because of this, it should be noted that material properties described are not those of pure drug melts or ionic liquids, but instead of melts or ionic liquids hydrates.

All stock solutions and powders used in the synthesis of the melts or ionic liquids were examined by proton nuclear magnetic resonance (NMR) and carbon NMR. The starting materials were used as acquired from the supplier without any further purification or modification with the exception of C4 which was freeze-dried to remove water from stock solution. C6 was also acquired as a water solution, but due to the highly hygroscopic nature of the material could not be freed of water even after multiple cycles of freeze-drying and thus was used as acquired to synthesize its corresponding propranolol melts or ionic liquid.

The products of the synthesis were also examined by proton NMR and carbon NMR. NMR verified successful synthesis of melts or ionic liquids. See FIGS. 1-5. 1:1 molar ratios of propranolol and dialkyl sulfosuccinates were also verified based on integration of assignable peaks in $^1H$ spectra. Unassigned peaks observed in starting components were also observed in final products; however, peak integration does not support enrichment of impurities in the final amorphous melts or ionic liquids compared to the starting materials.

The compositions confirmed with elemental analysis. Table 1 shows CHN elemental analysis of PFB and propranolol melt or ionic liquids. Samples were run in duplicate (n=2). Expected percent weights of pure substances are also listed.

The percentage weight of carbon, hydrogen and nitrogen as well as the carbon/nitrogen ratio were all within 3% of the expected values, which is in good agreement with purities of stock components. Three-percent impurities, corresponding to the expected impurity of PRL:Cl stock as well as from hydration of melts or ionic liquids, were taken into account when quantifying propranolol transport. Similar results were achieved for the free base.

TABLE 1

CHN elemental analysis of PFB and propranolol melts
Samples were run in duplicate (n = 2).
Supplementary Table 1 CHN elemental analysis of PFB and propranolol melts. Samples were run in duplicate (n = 2). Expected percent weights of pure substances are also given.

| | Weight Percent | | | | | | | |
|---|---|---|---|---|---|---|---|---|
| | C | | H | | N | | C/N Ratio | |
| Sample | Measured (n = 2) | Expected | Measured (n = 2) | Expected | Measured (n = 2) | Expected | Measured (n = 2) | Expected |
| PFB | 74.1 74.2 | 74.1 | 8.36 8.20 | 8.20 | 5.42 5.38 | 5.40 | 13.7 13.8 | 13.7 |
| PRL:C4 | 57.8 57.4 | 59.0 | 7.55 7.50 | 7.60 | 2.49 2.42 | 2.40 | 23.2 23.7 | 24.0 |
| PRL:C5 | 60.0 58.6 | 60.1 | 7.90 7.84 | 8.00 | 2.37 2.27 | 2.30 | 25.3 25.8 | 25.7 |
| PRL:C6 | 59.9 60.4 | 61.4 | 8.14 7.98 | 8.20 | 2.27 2.22 | 2.20 | 26.4 27.3 | 27.4 |
| PRL:C8 | 62.6 61.9 | 63.4 | 8.74 8.71 | 8.70 | 2.08 2.06 | 2.10 | 30.1 30.1 | 30.1 |

FIGS. 10A-10E indicate further characterization of propranolol melts or ionic liquids with ATR-FTIR. Dialkyl sulfosuccinates displayed a strong signal at ~1,730 $cm^{-1}$ corresponding to carbonyl stretching of the dialkyl sulfosuccinates as well as signal in the 1,100-1,300 cm$^{-1}$ range corresponding to sulfonate stretching modes. PFB and PRL:Cl displayed a broad, shallow signal at ~3,350 cm$^{-1}$ corresponding to the alcohol group. This peak was distinguishable from HOH stretching from residual water, which appears at ~3,500 cm$^{-1}$ in the C6 spectra shown in FIG. 10C. PFB and PRL:Cl also show a sharp, strong amine peak or two slightly overlapping amine peaks, respectively, at ~3,250 cm$^1$. The presence of a single NH stretching peak for PFB confirmed successful synthesis of free base. PFB and PRL:Cl also showed amine wagging and twisting peaks at ~764 and 787 cm$^{-1}$. All materials showed $CH_2$ and $CH_3$ stretching vibrations in the range 3,000-2,800 cm$^{-1}$. Propranolol melts or ionic liquids displayed vibrations characteristic of a combination of propranolol and dialkyl sulfosuccinate, including the alcohol group at ~3,350 cm$^{-1}$, CH stretching in the range 3,000-2,800 cm$^{-1}$, carbonyl stretching at 1,730 cm$^{-1}$, sulfonate stretching between 1,100-1,300 cm$^{-1}$, and amine wagging and twisting at 764 and 787 cm$^{-1}$. However, amine stretching peaks, c.a. 3,250 cm$^{-1}$, were repressed in the propranolol melts or ionic liquids. It is unclear why this peak was not detected in these materials as there is no indication from NMR that the molecular structure of propranolol has been affected.

This observation has been alleged to be an indication of salt formation in propranolol melts or ionic liquids with oleate as the counter species (see Crowley, K. J., et al., Oleate salt formation and mesomorphic behavior in the propranolol oleic acid binary system. *J. Pharm. Sci.* 88, 586-591 (1999), but could also simply be due to the unique local environment of hydrogen bond donors—acceptors or charged atoms in propranolol amorphous melts or ionic liquids compared to its crystalline forms. To glean some insight into whether propranolol exists as a hydrogen-bonded species or a fully protonated salt, the NH wagging and twisting peaks for the PFB, PRL:Cl and propranolol melts or ionic liquids were also compared (see FIG. 10E). Based on these peaks, salt formation is suggested by observation of a positive shift in wavenumber for the amine wagging and twisting peaks identified at peak positions 764 and 787 cm$^{-1}$. A positive shift of ~7 and ~9 cm$^{-1}$ at peak position 764 and 787 cm$^{-1}$, respectively, was observed for PRL:Cl and all propranolol melts or ionic liquids, while no shift was observed for PFB.

Thermogravimetric analysis (TGA) was performed to assess stability and purity (FIGS. 11A-11D). All amorphous melts or ionic liquids exhibited two-step decomposition. The first step occurred between 100-200° C. and is expected to be primarily water in accordance with Karl-Fischer titration, but could also be the release of some $CO_2$ from the decomposition of ester groups in dialkyl sulfosuccinate. Dialkyl sulfosuccinates exhibited decomposition at temperatures as low as 40° C. with multiple additional decomposition steps between 200-1,000° C. The extent of decomposition at each step seemingly decreases with increased dialkyl chain length. In contrast, PFB and PRL:Cl showed single step decomposition with the PRL:Cl salt being more resistant to decomposition than the crystalline free base, as expected. Rapid decomposition of propranolol melts or ionic liquids occurred at a similar temperature as was observed for PRL:Cl. Approximately 10% residual weight was observed upon combustion of all dialkyl sulfosuccinates, including melts or ionic liquids. It is unclear whether this is simply residual ash from dialkyl sulfosuccinate combustion or corresponds to some impurity; however, there were no significant unassignable peaks in the NMR spectra of the starting materials nor in the propranolol melts or ionic liquids which supports the former.

The melts or ionic liquids containing amorphous propranolol are provided in a form suitable for topical drug delivery. In some embodiments, the melts or ionic liquids containing amorphous propranolol is included in a topical drug delivery formulation. These formulations may be in any form suitable for application to the skin, such as in the form of a liquid, paste, ointment, cream, gel, foam, or lotion.

Optionally, the melts or ionic liquids containing amorphous propranolol are provided in a drug delivery patch to be applied to the skin. The patch typically contains adhesive on one side, i.e. the side that is placed in contact with the skin. The melts or ionic liquids containing amorphous propranolol may be included in the adhesive, such as in the form of a solution or a dispersion.

The adhesive can be any suitable known adhesive that is used in drug delivery patches for application to the skin. In some forms, the adhesive can include polymers. The polymers can be cross-linked or uncross-linked. Exemplary polymers include, but are not limited to, poly[acrylic acid-co-butylacrylate-co-(2-ethylhexyl)acrylate-co-vinylacetate], poly(acrylic acid), sodium alginate, carboxymethylcellulose, hydroxymethylcellulose, polyanhydrides, and methylcellulose.

The drug delivery formulation or patch contains a sufficient amount of the amorphous propranolol to deliver a therapeutically effective amount of the amorphous propranolol to the patient in need of treatment, such as for the treatment or amelioration of infantile hemangioma. Typically, the therapeutically effective amount of propranolol for the treatment or amelioration of infantile hemangioma is in the range of about 0.1 mg to 10 mg. The formulation or patch typically contains at least 10% in excess of the therapeutically effective amount to be delivered to the patient, optionally the formulation or patch contains even greater amounts, such as 10-20% in excess, 10-50% in excess, 20-50% in excess, 30-50% in excess, 40-50% in excess of the amount to be delivered to the patient or even up to 100% in excess, such as 90-100% in excess, 80-90% in excess, 70-90% in excess, or 60% to 90% in excess of the amount to be delivered to the patient. The amount of propranolol in the formulation or patch is a function on the particular formulation or patch and its efficiency in delivering the amorphous propranolol to the patient.

Typical viscosities for the transdermal drug delivery formulations described herein range from 0.01 to 10 centipoise (cP) when measured at 37° C., typically the viscosity is within the range of 0.01 to 10 cP when measured at 25° C. Optionally the viscosity of the formulation is in the range of 0.01 to 1 cP, 0.01 to 1 cP, or 0.1 to 1 cP. The viscosity can be measured using any suitable rheometer, such as for example as described herein using 1-mL samples with a LC-ARES Test Station (TA Instruments, New Castle, Del.) and a cone (diameter: 25 mm; angle: 0.1 rad), with a cone rotation rate of 10 s$^{-1}$.

The molecular weights of propranolol melts or ionic liquids ranged from 569.71 to 681.92 depending on that of the counter species, and the densities of the formulations were about 1.2 g/mL and changed little between the counter species (FIG. 6A). Since conductivity is concentration dependent, measured conductivity was normalized by molar concentration. The molar conductivities of "neat" propranolol melts or ionic liquids at 25° C. were less than $1.5 \times 10^{-4}$ S cm$^2$/mol (FIG. 6B). As expected, conductivities of neat melts or ionic liquids at 37° C. were higher than those at 25°

C.; however, they do not seem to depend on the carbon chain length of the counter species.

In contrast, the viscosities of neat propranolol melts or ionic liquids at 25° C. varied significantly with counter species (59.5-1,889.4 Pa·S), and this trend was observed at 37° C. as well. Table 2 shows viscosities of propranolol melts or ionic liquids measured at 25° C. and 37° C. Standard deviations of three measurements are provided in parentheses. The viscosity of topical formulations influences ease of handling, and PRL:C5 and PRL:C8 were easy to handle without any addition of solvent or excipients.

TABLE 2

Viscosities of Propanolol Melts measured at 25° C. and 37° C. Supplementary Table 2 Viscosities of propranolol melts measured at 25° C. and 37° C. SD of three measurements in parentheses. Propranolol Melt Viscosity

| | Pa s | |
|---|---|---|
| | 25° C. | 37° C. |
| PRL:C4 | 599.5 (6.5) | 87.0 (0.7) |
| PRL:C5 | 59.5 (1.6) | 14.7 (0.2) |
| PRL:C6 | 1889.4 (325.2) | 180.9 (10.8) |
| PRL:C8 | 70.4 (0.9) | 16.9 (0.1) |

Differential scanning calorimetry (DSC) measurement showed that all propranolol melts or ionic liquids possessed a glass transition peak (PRL:C4; −18° C., PRL:C5; −21° C., PRL:C6; −9° C., PRL:C8; −24° C.), further confirming their amorphous nature under biologically relevant conditions. A crystallization peak and melts or ionic liquiding peak were not detected (FIGS. 12A-12D). These results are in good agreement with other amorphous melts or ionic liquids of active pharmaceutical ingredients (APIs) and dialkyl sulfosuccinate reported in the literature. See Hough, W. L. et al. The third evolution of ionic liquids: Active pharmaceutical ingredients. $N. J. Chem.$ 31, 1429 (2007); Cojocaru, O. A. et al. Prodrug ionic liquids: Functionalizing neutral active pharmaceutical ingredients to take advantage of the ionic liquid form. $MedChemComm.$ 4, 559-563 (2013). In comparison, PRL:Cl has a melting point of 164° C., C8 has a melting point of 153° C., while PFB has a melting point of 96° C.

Lipophilicity of propranolol melts or ionic liquids, measured as partition coefficient n-octanol/water (log $P_{o/w}$), varied depending on the carbon chain length of the counter species (FIG. 6C). The log $P_{o/w}$ of propranolol melts or ionic liquids ranged from 0.76 to 1.76, and were between −0.41 of PRL:Cl and 3.12 of PFB.

Figures 7A, 7B, 7C, 7D:
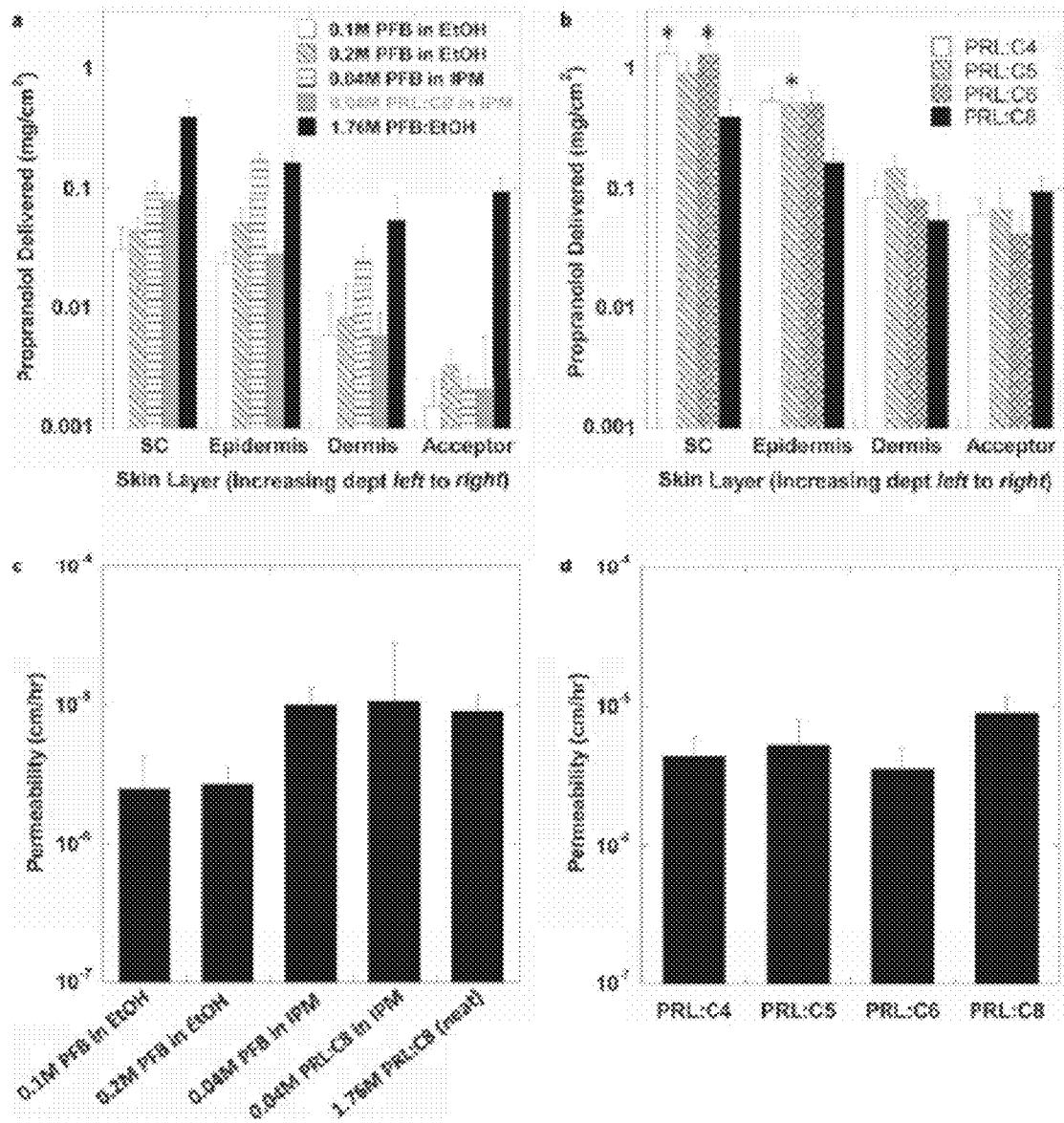
FIGS. 7A-7D are bar charts showing skin transport of propranolol melts or ionic liquids and PFB in organic solvent.

Skin transport ability of propranolol melts or ionic liquids: Since the amount of skin irritation caused by a topical drug formulation is irrelevant if the formulation does not result in a therapeutically viable dose delivered, transport of propranolol through the skin was evaluated first. To examine the ability of propranolol melts or ionic liquids to penetrate skin compared with PFB, skin transport tests using porcine skin were conducted (FIGS. 7A and 7B). PRL:C8 was of particular interest for skin transport from the perspective of its low viscosity and conductivity. PFB was used near the limit of solubility in both ethanol (EtOH, soluble ≤0.4 M) and isopropyl myristate, IPM, soluble ≤0.06 M). PRL:C8 yielded delivery enhancement into each layer compared to 0.1 M or 0.2 M PFB in EtOH (FIG. 7A). The amounts of propranolol delivered from PRL:C8 were also greater than those delivered by a solution of PFB in IPM, a known chemical penetration enhancer. As an additional control PRL:C8 was dissolved in IPM and delivery of propranolol was measured. The amount delivered from an IPM solution of PRL:C8 was lower than that from neat PRL:C8, but still comparable to that of PFB dissolved in IPM. All neat amorphous melts or ionic liquids in addition to PRL:C8 also exhibited skin penetration of propranolol (FIG. 7B). The amounts of propranolol delivered in the stratum corneum (SC) and epidermis by PRL:C8 were less than those by other melts or ionic liquids. However, the delivered amount of propranolol into acceptor from PRL:C8 was equal to or greater than that from other melts or ionic liquids. To determine if enhanced transport of propranolol across the skin was simply due to the higher applied concentration afforded by propranolol melts or ionic liquids compared to PFB in an organic solvent, skin permeabilities corresponding to each formulation were determined (FIGS. 7C and 7D). The permeabilities of all propranolol melts or ionic liquids were comparable to PFB in both EtOH and IPM with no statistically significant differences observed. In other words, propranolol melts or ionic liquids afforded increased drug flux due to higher applied concentrations but did not significantly enhance nor reduce the efficiency of drug transport. PFB permeability in IPM did appear to be slightly enhanced compared to EtOH (FIG. 7C), although differences in permeabilities were not statistically significant. Similarly, the permeabilities associated with neat PRL:C8 and PRL:C8 in IPM were comparable and appear to be slightly higher than those from PFB in ethanol (FIG. 7C). No significant variation of permeabilities was found among various neat propranolol melts or ionic liquids (FIG. 7D).

Skin Irritation Potential of Propranolol Melts or Ionic Liquids

Since propranolol melts or ionic liquids were found to result in significant drug delivery through the skin, the skin irritation potentials of PRL:C8 and PRL:C5 were evaluated and compared to that of PFB in EtOH. These melts or ionic liquids were chosen because of their excellent delivery potential and low viscosities, thus offering ease of handling. Evaluation was conducted using human skin equivalent tissues (Epiderm™) with a human interleukin-1α ELISA kit. Interleukin-1α release has been previously established as an indicator for skin irritation and affords evaluating irritation without requiring removal of the test formulation from skin tissues, a potentially damaging process to the tissues when studying viscous formulations. 0.1 M and 0.2 M PFB EtOH formulations, positive control (5% sodium dodecyl sulfate (SDS) in PBS), negative control (PBS) and EtOH solvent control were also evaluated.

Figures 8A, 8B:
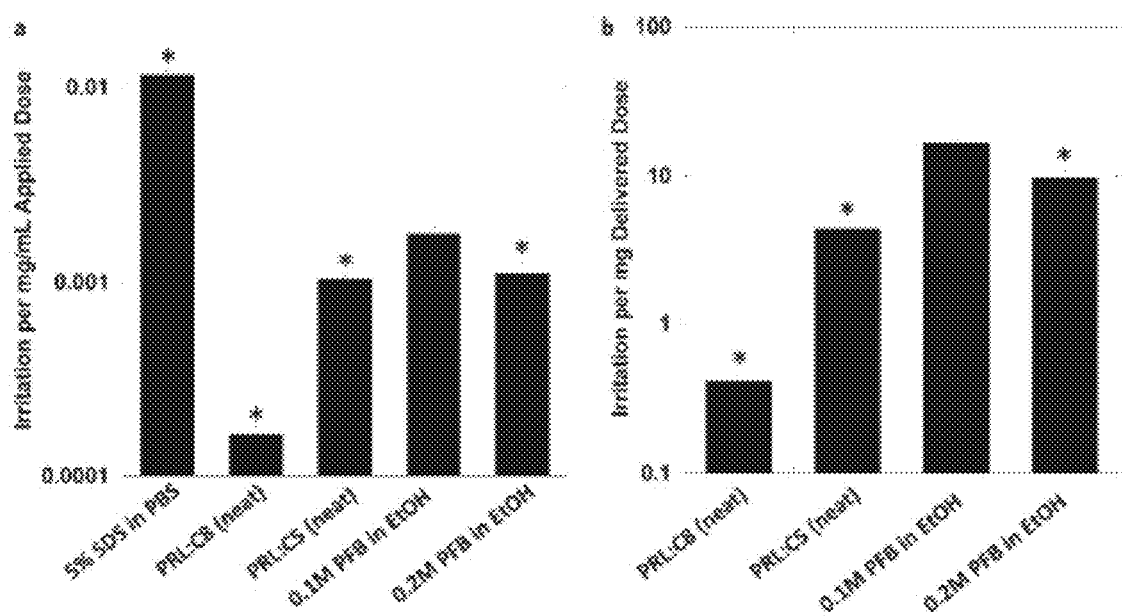
FIGS. 8A and 8B are bar charts showing skin irritation potential using Mat Tek Epiderm™ human skin equivalent tissues. Interleukin-1α release was used as an indicator of irritation.
Figures 14A, 14B:
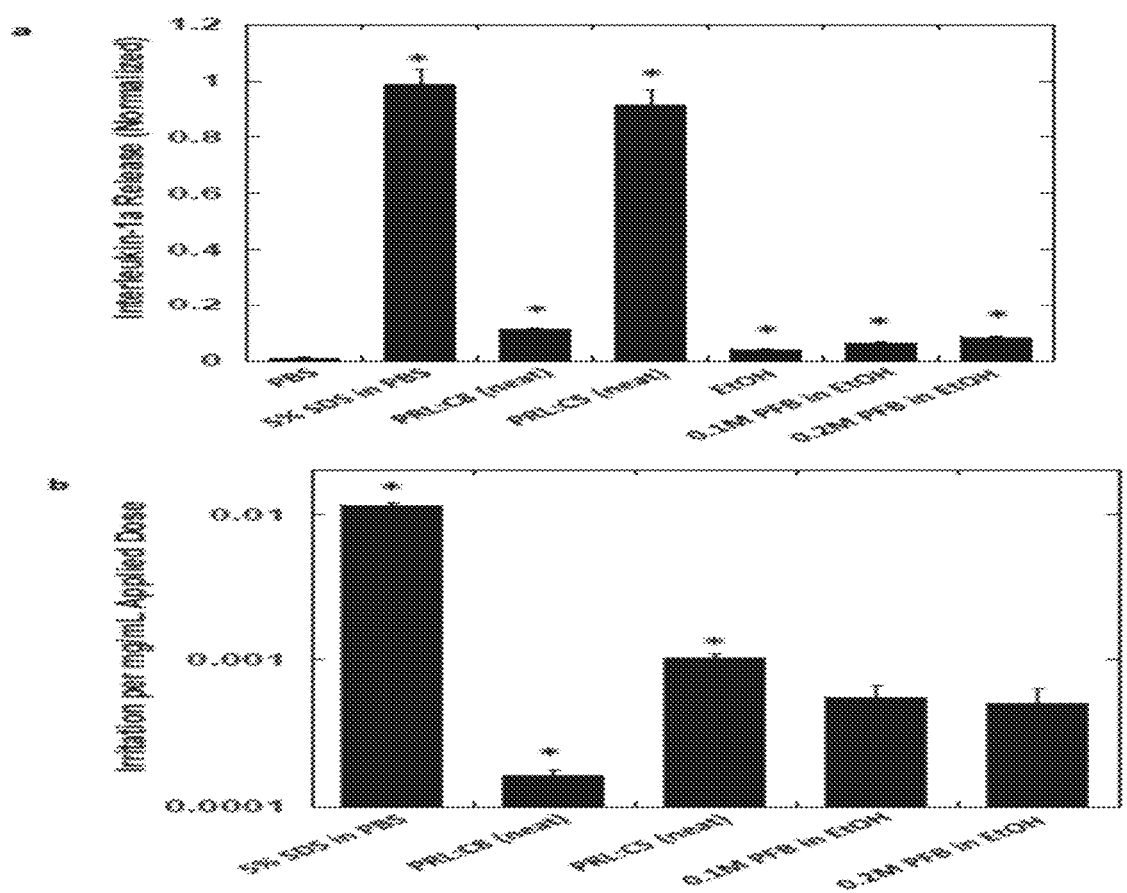
FIGS. 14A and 14B are bar graphs showing skin irritation using Mat Tek Epiderm™ human skin equivalent tissues.

Interleukin-1α release varied significantly between the formulations (FIG. 14A). The negative control (PBS) showed negligible irritation while the positive control (5% SDS in PBS) resulted in the highest amount of irritation (FIG. 14A). To compare irritation potentials of propranolol melts or ionic liquids applied neat to those of PFB in EtOH, the measured irritation was divided by the applied dose (FIG. 8A). Dose-normalized skin irritation potential of PRL:C8 was 11-fold lower than that of 0.1 M PFB EtOH formulation (p=0.014). In addition, skin irritation potential of PRL:C5 was 1.7 times lower than that of 0.1 M PFB EtOH formulation (p=0.0049). In an attempt to isolate the contribution of the drug and the solvent, irritation potential of EtOH solvent control was subtracted from that of PFB EtOH formulations (FIG. 14B) and the conclusions of such normalized irritation potential were generally the same as those shown in FIG. 8A. Normalization of skin irritation potential was also assessed based on the delivered dose in the acceptor compartment (FIG. 8B). Once again, similar conclusions were reached. Specifically, irritation potential of PRL:C8 was 40-fold lower compared to that of 0.1 M PFB EtOH formulation (p=0.0085) and skin irritation potential of PRL:C5 was 3.7 times lower than that of 0.1M PFB EtOH formulation (p=0.00026).

Molar Conductivity of ILs in Water and n-Octanol

Figures 9A, 9B:
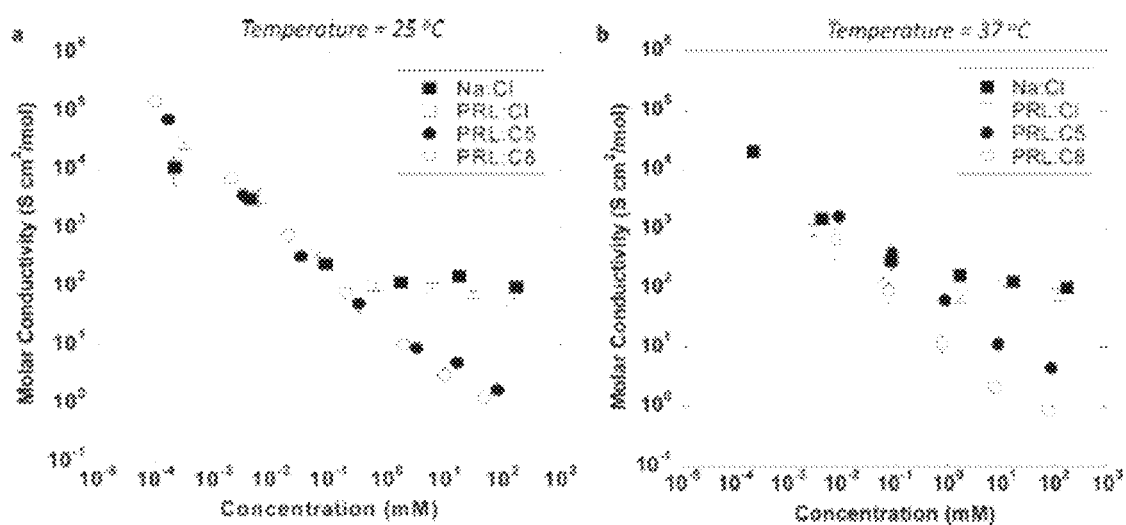
FIGS. 9A and 9B are graphs showing molar conductivities (S cm$^2$/mol) of propranolol melts or ionic liquids. Molar conductivities of propranolol melts or ionic liquids in water were measured at 25° C.
Figure 10A:
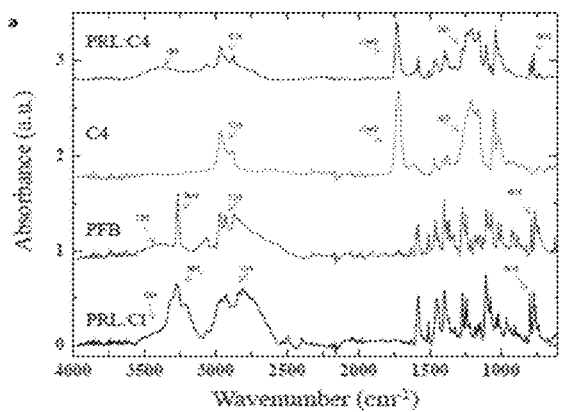
FIGS. 10A-10E are line graphs showing attenuated total reflection Fourier transform infrared spectroscopy (ATR-FTIR) spectra of all starting materials, PFB, and propranolol melts or ionic liquids.
Figure 10B:
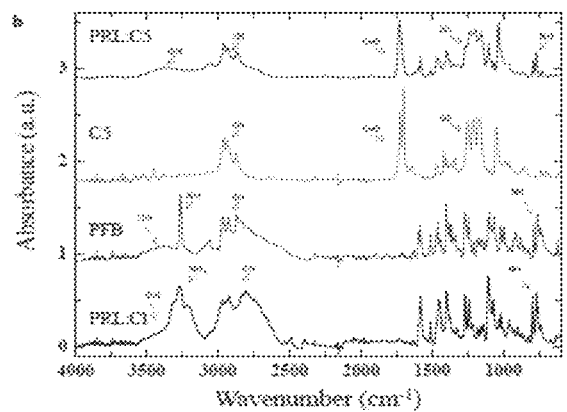
Figure 10C:
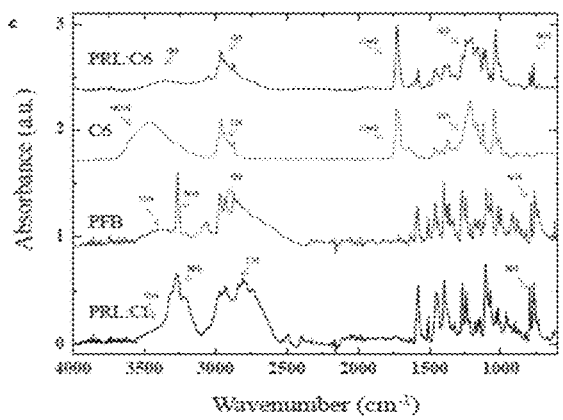
Figure 10D:
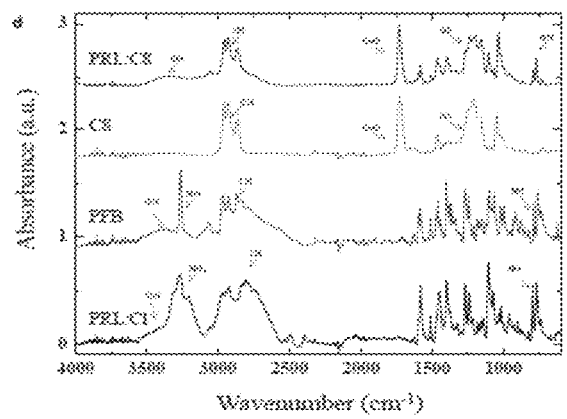
Figure 10E:
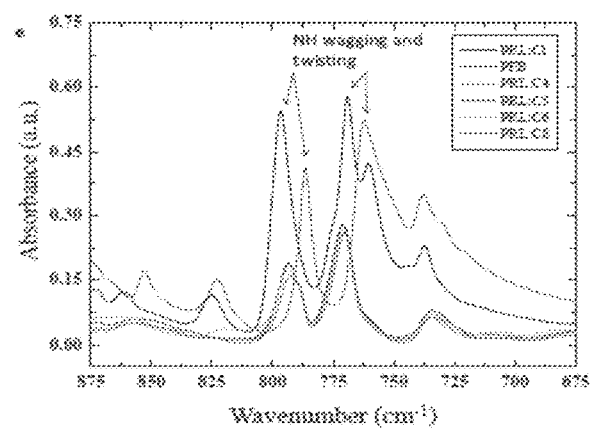
Figure 11A:
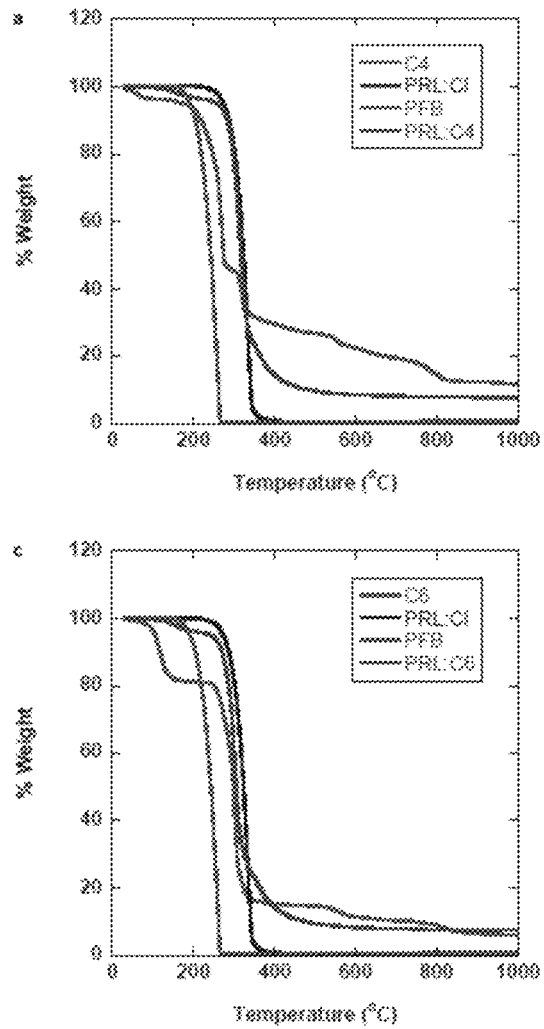
FIGS. 11A-11D are line graphs showing thermogravimetric analysis (TGA) of all starting materials, PFB and propranolol melts or ionic liquids.
Figure 11B:
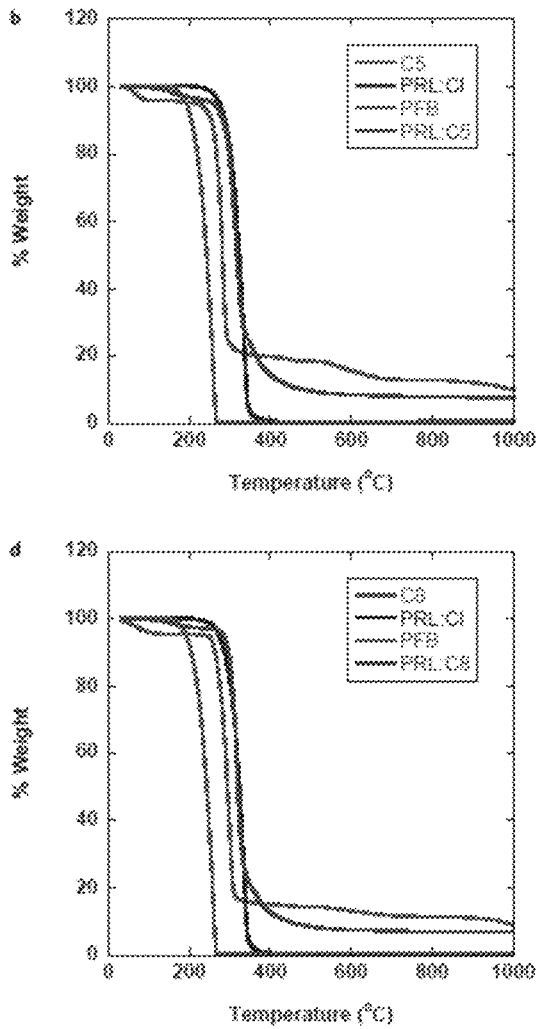
Figure 11C:
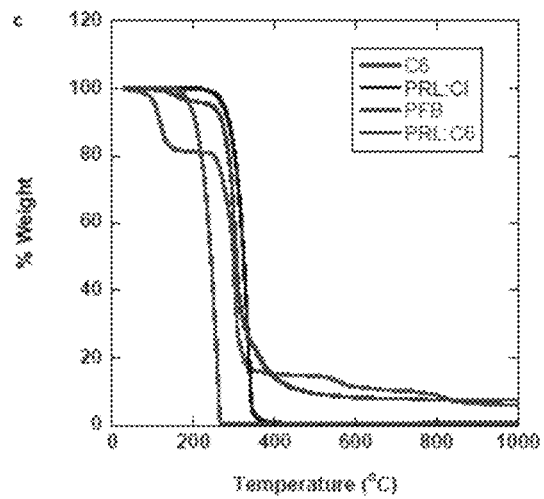
Figure 11D:
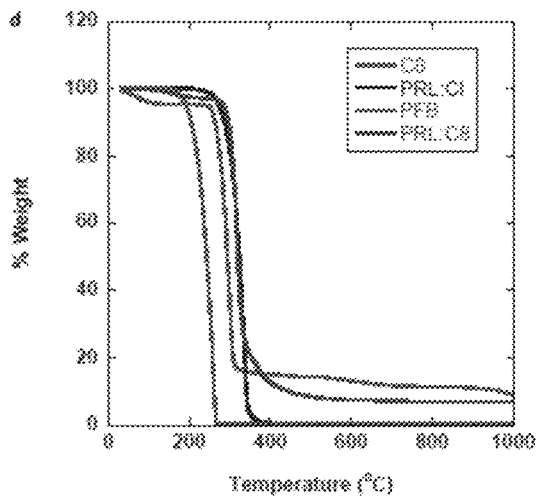
Figures 13A, 13B:
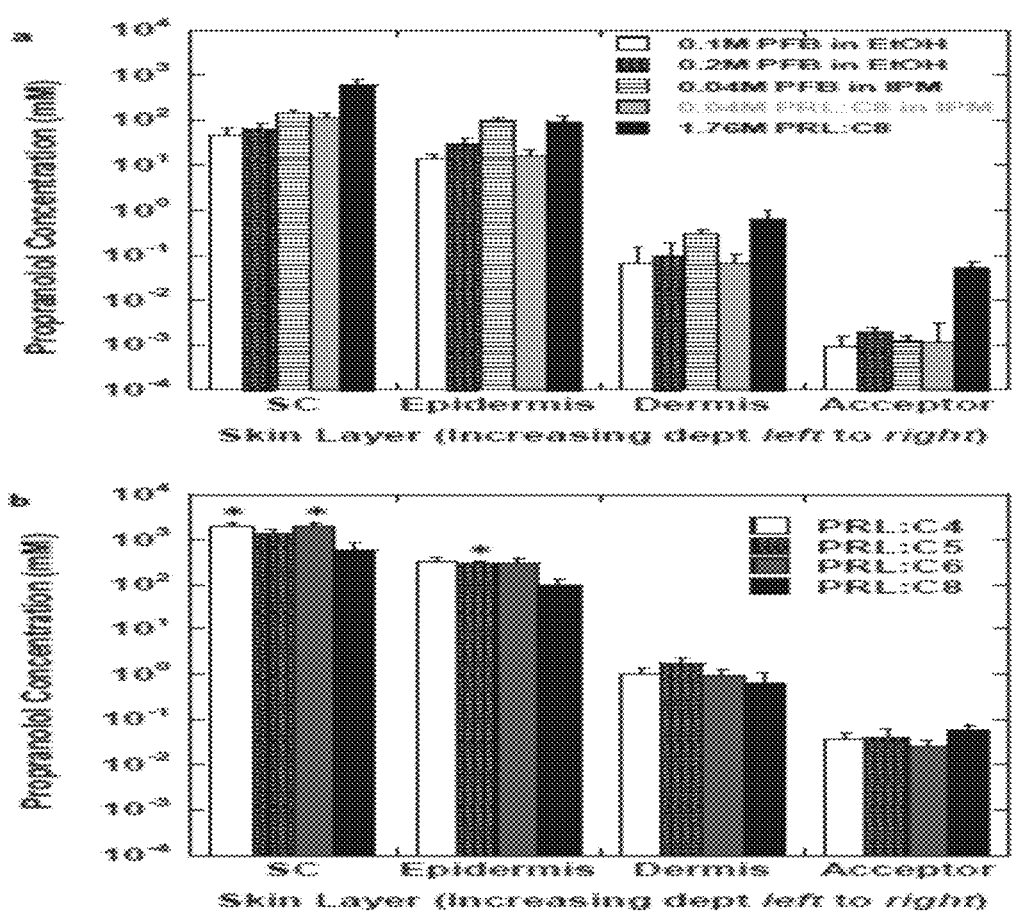
FIGS. 13A and 13B are bar graphs showing propranolol concentrations delivered into individual layers of porcine skin. Concentration of propranolol delivered in whole stratum corneum (SC), epidermis, dermis and acceptor was estimated using the experimentally determined dose delivered and the average thickness of porcine skin layers, as described in Bronaugh, R. L., et al., Methods for in vitro percutaneous absorption studies II. Animal models for human skin. Toxicol. Appl. Pharmacol. 62, 481-488 (1982). Delivery depth increases from left to right.

Skin irritation potential of PRL:C8 compared to PFB EtOH formulations was reduced remarkably. In contrast, skin irritation potential of PRL:C5 showed little reduction compared to the PFB. To investigate the possible mechanism of the difference in skin irritation potential, molar conductivities in water of the amorphous melts or ionic liquids as well as sodium chloride (Na:Cl) and propranolol hydrochloride (PRL:Cl) were investigated (FIGS. 9A and 9B). When conductivities were measured at 25° C. (FIG. 9A), molar conductivities of Na:Cl and PRL:Cl showed similar behavior at all concentrations studied. Similarly, molar conductivity of PRL:C8 was comparable to that of PRL:C5 over the entire range, and melts or ionic liquids showed similar behavior to Na:Cl at concentrations less than $10^{-1}$ mM. At 37° C. (FIG. 9B), however, molar conductivity of PRL:C5 was significantly higher than that of PRL:C8 at concentrations over $10^{-1}$ mM. This result indicates PRL:C5 dissociates to a greater extent than PRL:C8 at concentrations that are expected in viable epidermis and dermis (FIG. 13B). Molar conductivities of propranolol melts or ionic liquids were also measured in n-octanol to assess dissociation of propranolol and dialkyl sulfosuccinate in a hydrophobic environment similar to skin lipid channels. Mean±SD molar conductivities of 1.32 mM PRL:C8 in n-octanol were 0.49±0.01 and 0.51±0.01 S cm$^2$/mol at 25° C. and 37° C., respectively. Mean±SD molar conductivities of 1.24 mM PRL:C5 in n-octanol were 0.35±0.01 and 0.40±0.01 S cm$^2$/mol at 25° C. and 37° C., respectively.

Propranolol was formulated as amorphous melts or ionic liquids by salt metathesis between propranolol hydrochloride and sodium dialkyl sulfosuccinate (See Scheme 1). The resulting propranolol melts or ionic liquids were described with NMR (FIGS. 1 to 5) and ATR-FTIR (FIGS. 10A-10E) and possessed both transparency and fluidity at room temperature. Transparency and fluidity was retained after removal of residual water under vacuum with repeated purging with nitrogen thus confirming the synthesis of amorphous melts or ionic liquids and not simply concentrated water solutions. However, water is quickly absorbed upon exposure to atmosphere and thus all characterization and experiments were performed with propranolol melts or ionic liquid hydrates (referred to herein as simply propranolol melts or ionic liquids). The expected impurity of the propranolol stock as well as the measured amount of hydration were taken into account for all transport and irritation studies.

Propranolol melts or ionic liquids afforded concentrated topical formulations in excess of what is possible for PFB or PRL:Cl in organic or aqueous solvents. Specifically, melts or ionic liquids possessed sufficiently low viscosity to be applied directly to the skin without any addition of solvent, affording concentrations in excess of 1.76 M on the surface of the skin. In contrast, PFB solubility in EtOH and IPM was limited to 0.4 M and 0.06 M, respectively. Concurrently, the solubility of PRL:Cl in water and methanol was limited to 0.17 M and 0.51 M, respectively. The advantage of propranolol melts or ionic liquids compared to organic formulations of PFB for drug delivery through the skin was demonstrated by measuring transport across porcine skin (FIGS. 7A-7D). The concentrated nature of propranolol melts or ionic liquids afforded >30-fold increase in propranolol flux across the skin compared to PFB formulated near saturation in either EtOH or IPM (FIGS. 7A and 7B). Moreover, the efficiency of drug transport was comparable among all formulations tested (FIG. 7D). Specifically, permeabilities, defined here as flux normalized by the applied dose, showed no statistically significant differences in delivery efficiency. In fact, PRL:C8 exhibited slightly higher permeability compared to that from PFB-EtOH formulations. Other propranolol melts or ionic liquids also exhibited slightly higher permeabilities than EtOH formulations, however, PRL:C8 showed the highest permeability among analog melts or ionic liquids.

PRL:C8 also exhibited a marked reduction in irritation potential (FIGS. 8A and 8B). This is the first study of skin irritation of amorphous melts or ionic liquids containing propranolol. Although irritation from neat melts or ionic liquids (PRL:C8 and PRL:C5) was observed to some extent, dose-normalized skin irritation of PRL:C8 was found to be significantly lower than that of PFB (FIG. 14B). This trend, however, was not observed for both amorphous melts or ionic liquid formulations tested; dose-normalized irritation potential of PRL:C5 was only slightly reduced compared to EtOH formulations of PFB (FIGS. 8A and 8B).

In the analysis of propranolol delivery into the skin, only delivery of propranolol (not delivery of dialkyl sulfosuccinate) was quantified. However, the mechanism of reduced irritation was also explored by considering whether the two counter species are transported through the skin together as a complex or as separate species (equimolar or otherwise). To glean insight into the transport of propranolol and its corresponding counter species, the molar conductivity of PRL:C8 and PRL:C5 was quantified at various concentrations and in both water (to simulate aqueous environments like the epidermis, dermis, and systemically) and octanol (to simulate the SC). Molar conductivities were evaluated for concentrations expected in the skin based on the average thickness of porcine skin layers as described in Bronaugh, R. L., et al., Methods for in vitro percutaneous absorption studies II. Animal models for human skin. Toxicol. Appl. Pharmacol. 62, 481-488 (1982) and based on the experimentally determined dose delivered. Molar conductivity is commonly used as a measure for ion association in solution. In comparison to sodium chloride, which completely dissociates in water, PRL:C5 and PRL:C8 had a much lower molar conductivity at concentrations >0.1 mM (FIGS. 9A and 9B). This suggests the counter species in propranolol melts or ionic liquids remain relatively associated at concentrations expected in the viable epidermis and dermis (FIGS. 13A and 13B), where skin inflammation typically presents. In contrast, PRL:Cl possessed similar molar conductivity to sodium chloride for all concentrations which indicates complete disassociation of PRL:Cl in the viable epidermis and dermis.

Counter species association was not identical between different propranolol melts or ionic liquids which may provide some insight into the stark contrast in dose-normalized skin irritation resulting from PRL:C8 compared to PRL:C5 (FIGS. 8A and 8B). Specifically, at 37° C. PRL:C8 had ~10-fold lower molar conductivity than PRL:C5 at concentrations >1 mM (FIG. 9B). This result suggests propranolol formulated as an amorphous melt or ionic liquid with dioctyl sulfosuccinate affords a higher degree of counter species association in the skin compared to propranolol formulated with diamyl sulfosuccinate. This result corresponds well with the ~10-fold observed difference in skin irritation potential between PRL:C8 and PRL:C5 (FIGS. 8A and 8B). On the other hand, both melts or ionic liquids are expected to dissociate in plasma at effective plasma concentrations of 3-100 ng/mL (see Pine, M., et al., Correlation of plasma propranolol concentration with therapeutic response in patients with angina pectoris. *Circulation* 52, 886-893 (1975)) corresponding to $1\times10^{-5}$ to $4\times10^{-4}$ mM because molar conductivities in water of both propranolol melts or ionic liquids showed similar behavior to PRL:Cl at concentrations less than $10^{-1}$ mM. Therefore, it is expected that the therapeutic activity of propranolol will be substantially the same when formulated as a melt or ionic liquid. Association in the SC would be expected to be even stronger due to the much lower dielectric constant of the SC lipids (modeled with octanol) in combination with higher concentrations in the SC compared to the dermis (FIGS. 13A and 13B). This was confirmed experimentally as the molar conductivity of propranolol melts or ionic liquids in octanol were roughly 100-fold lower than that of melts or ionic liquids in water. Therefore, the two counter species in propranolol melts or ionic liquids are likely to traverse through the SC lipids as a pair.

The studies reported here indicate that propranolol melts or ionic liquids can possess safely and effectively deliver propranolol across the skin.

Results of this study show propranolol melts or ionic liquids, when topically applied to the skin, successfully deliver propranolol through the skin and can afford reduced skin irritation potential compared to traditional PFB formulations in organic solvent.

Transdermal delivery devices may be used for the delivery of formulations of amorphous propranolol melts or ionic liquids. The transdermal delivery formulations may further contain inactive ingredients that enhance long-term shelf storage or target area absorption. Such inactive ingredients include, but are not limited to, emollient/stiffening agents/ ointment bases such as carnauba wax, cetyl alcohol, cetyl ester wax, emulsifying wax, hydrous lanolin, lanolin, lanolin alcohols, microcrystalline wax, paraffin, petrolatum, polyethylene glycol and polymers thereof, stearic acid, stearyl alcohol, white wax, and yellow wax; an emulsifying agent/ solubilizing agent such as polysorbate 20, polysorbate 80, polysorbate 60, poloxamer, emulsifying wax, sorbitan monostearate, sorbitan monooleate, sodium lauryl sulfate, propylene glycol monostearate, diethylene glycol monoethyl ether, docusate sodium; a humectant such as glycerin, propylene glycol, polyethylene glycol, sorbitol solution, and 1,2,6-hexanetriol; thickening/gelling agents such as carbomer, methyl cellulose, sodium carboxyl methyl cellulose, carrageenan, colloidal silicon dioxide, guar gum, hydroxypropyl cellulose and polymers thereof, hydroxypropyl methyl cellulose, gelatin, polyethylene oxide, alginic acid, sodium alginate, and fumed silica; a preservative such as benzoic acid, propyl paraben, methyl paraben, imidurea, sorbic acid, potassium sorbate, benzalkonium chloride, phenyl mercuric acetate, chlorobutanol, and phenoxyethanol; permeation enhancers such as propylene glycol, ethanol, isopropyl alcohol, oleic acid, polyethylene glycol; chelating agent such as ethylene diamine tetraacetate; antioxidants such as butylated hydroxyanisole and butylated hydroxytoluene; acidifying/alkalizing/buffering agents such as citric acid, phosphoric acid, sodium hydroxide, monobasic sodium phosphate, and trolamine; and vehicles/solvents such purified water, hexylene glycol, propylene glycol, oleyl alcohol, propylene carbonate, and mineral oil. Additional inactive ingredients that may be included in the transdermal delivery devices, include for example, acrylate or acrylates, including polymers thereof, methacrylate or methacrylates, including polymers thereof, cellulose polymers, hydroxyethyl cellulose and polymers thereof, poly-lactylate polymers, polyvinyl pyrrolidone polymers, ethylenevinylacetate copolymers, short, medium and long chain fatty acid molecules and analogs thereof, isopropryl myristate, polyethylene terephthalate, vitamin C, vitamin C analogs or esters, vitamin E, vitamin E analogs, vitamin E polymeric compounds, d-α-tocopheryl polyethylene glycol 1000 succinate (vitamin E TPGS) and silicone. Many excipients of these excipients possess dual or multiple functionalities. For example polyethylene glycol is an emollient, humectant, and a permeation enhancer.

Lipophilicities of propranolol melts or ionic liquids, described as log $P_{o/w}$, were in the range of 1 and 3 which makes them suitable for traversing the lipophilic SC and the aqueous layers such as epidermis and dermis for systemic delivery. Brown, et al., Dermal and transdermal drug delivery systems: Current and future prospects. *Drug Deliv.* 13, 175-187 (2006).

The API—melt or ionic liquid is able to transport through lipophilic SC and remain complexed in viable epidermis and dermis. Without being bound by theory, it is believed that the extent of complexation in the epidermis and dermis affects the extent of skin irritation elicited by the API. Eventually, however, the API fully dissociates in systemic circulation to prevent neutralization of the API by the counter species at the target receptor. PRL:C8 possessed higher lipophilicity than PRL:C5 which may drive ion association within the epidermis and dermis, while PRL:C5 most likely dissociates once it transports through the SC. On the other hand, if lipophilicity is too great there may not be adequate partitioning from the SC into the epidermis. Alternatively, the extent of ionic interactions may affect the extent of skin irritation elicited by the API.

The amount of hydration can affect the extent of skin irritation. In this study, propranolol melt or ionic liquid hydrates which were composed of roughly 2-3% residual water were used.

Propranolol melts or ionic liquids deliver a significant drug dose into the skin and afford higher flux rates compared to free base in organic solvent. Flux rates for the melts and ionic liquids containing propranolol can range from 0.01 mg/cm$^2$ to 10 mg/cm$^2$. Propranolol melts or ionic liquids, synthesized and applied as described, can result in reduced skin irritation. Reduction in irritation was not found to be ubiquitous among melts or ionic liquids tested. Instead, irritation appears to be negatively proportional to counter species association in conditions expected in the skin, i.e., the greater the extent of counter species association the less irritation was observed. It can be understood from the disclosure that additional stabilized ionic liquid forms of propranolol analog compounds may be used to treat diseases, for example, infantile hemangioma. In addition, the compounds described herein include:

a compound of formula (I)

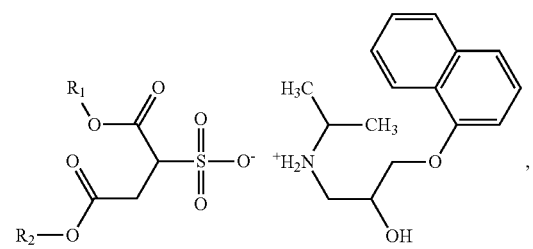

Formula I wherein

R$_1$ and R$_2$ are each independently an unsubstituted alkyl, substituted alkyl, substituted alkenyl, unsubstituted alkenyl, substituted alkynyl, unsubstituted alkynyl, unsubstituted aryl, substituted aryl, substituted heteroaryl, unsubstituted heteroaryl, substituted C$_3$-C$_{20}$ cycloalkyl, unsubstituted C$_3$-C$_{20}$ cycloalkyl, substituted polyaryl, unsubstituted polyaryl, substituted polyheteroaryl, unsubstituted polyheteroaryl, substituted C$_3$-C$_{20}$ heterocyclyl, unsubstituted C$_3$-C$_{20}$ heterocyclyl, substituted C$_3$-C$_{20}$ cycloalkenyl, unsubstituted C$_3$-C$_{20}$ cycloalkenyl, substituted C$_3$-C$_{20}$ cycloalkynyl, or unsubstituted C$_3$-C$_{20}$ cycloalkynyl.

In some aspects, R$_1$ and R$_2$ are each independently unsubstituted C$_3$-C$_{14}$ alkyl groups or substituted C$_3$-C$_{14}$ alkyl groups.

In some aspects, R$_1$ and R$_2$ are each independently a substituted C$_3$ alkyl group, unsubstituted C$_5$ alkyl group, unsubstituted C$_6$ alkyl group, unsubstituted C$_7$ alkyl group, or unsubstituted C$_8$ alkyl group.

In some aspects, R$_1$ and R$_2$ are both substituted C$_3$ alkyl groups, unsubstituted C$_5$ alkyl groups, unsubstituted C$_6$ alkyl groups, unsubstituted C$_7$ alkyl groups, or unsubstituted C$_8$ alkyl groups.

The compound of formula (I) can be a melt or ionic liquid. The melt or ionic liquid of the compound of formula (I) may be formed by a salt metathesis reaction. The salt metathesis reaction can involve reacting propranolol hydrochloride with an alkali metal dialkyl sulfosuccinate, such as a sodium dialkyl sulfosuccinate. For example, the alkali metal dialkyl sulfosuccinate can be sodium diisobutyl sulfosuccinate, sodium diamyl sulfosuccinate, sodium dihexyl sulfosuccinate, or sodium dioctyl sulfosuccinate.

Other beta blockers can be used in place of propranolol in the ionic liquids or melts, compounds, topical formulations or patches, and/or methods described herein. For example, the ionic liquid or melt may contain another beta blocker in place of propranolol. Optionally, the compound of formula (I) may contain another beta blocker in place of propranolol. Thus, the compound could be formed from another beta blocker with sodium dialkyl sulfosuccinate. The topical drug delivery formulation may contain the melt or ionic liquid of another beta blocker. The method of use may include topically applying the formulation containing the melt or ionic liquid of another beta blocker to transdermally deliver a beta blocker to a patient in need thereof or applying a patch to the skin where the patch contains the melt or ionic liquid of another beta blocker in place propranolol, as described above. The formulation or patch containing the formulation may be applied at the site in need of treatment, such as the site of a skin lesion.

The beta blocker can be a beta-receptor blocking agent, a beta-adrenergic receptor blocking agent, a beta blocking agent, beta-blocking agent or beta-adrenergic receptor blocking agent or any other phrase indicating a chemical that inhibits the binding of agonists, natural or artificial, to beta-adrenergic receptors of any type (beta-1, beta-2, beta-3 or others). The beta blocker may be a non-selective beta blocker, a beta-1-selective beta blocker, a mixture of alpha-1/beta-adrenergic antagonists, a beta-2-selective beta blocker.

Examples of other beta blockers, besides propranolol, that may be used are disclosed in Goodman and Gilman's the pharmacological basis of therapeutics, eleventh edition, chapter 10, pp 271-295, 2006. Suitable non-selective beta blockers included, but are not limited to alprenolol, bucindolol, carteolol, carvedilol, labetalol, levobunolol, medroxalol, mepindolol, metipranolol, nadolol, oxprenolol, penbutolol, pindolol, propafenone (propafenone is a sodium channel blocking drug that also is a beta-adrenergic receptor antagonist), sotalol, timolol, pharmaceutically acceptable salts thereof, or combinations thereof. Suitable beta-1 selective beta blockers include, but are not limited toacebutolol, atenolol, betaxolol, bisoprolol, celiprolol, esmolol, metoprolol, nebivolol, or combinations thereof. The beta blocker may also have an intrinsic sympathomimetic activity, for example acebutolol, betaxolol, carteolol, carvedilol, labetalol, oxprenolol, penbutolol, and pindolol.

Any of the beta-blockers described herein can be used alone or in combination with any of the other beta-blockers as well.

Methods

All chemical reagents and solvents were obtained from commercial sources and used without further purification. All measurements were conducted at 25° C. unless noted otherwise.

Figure 2:
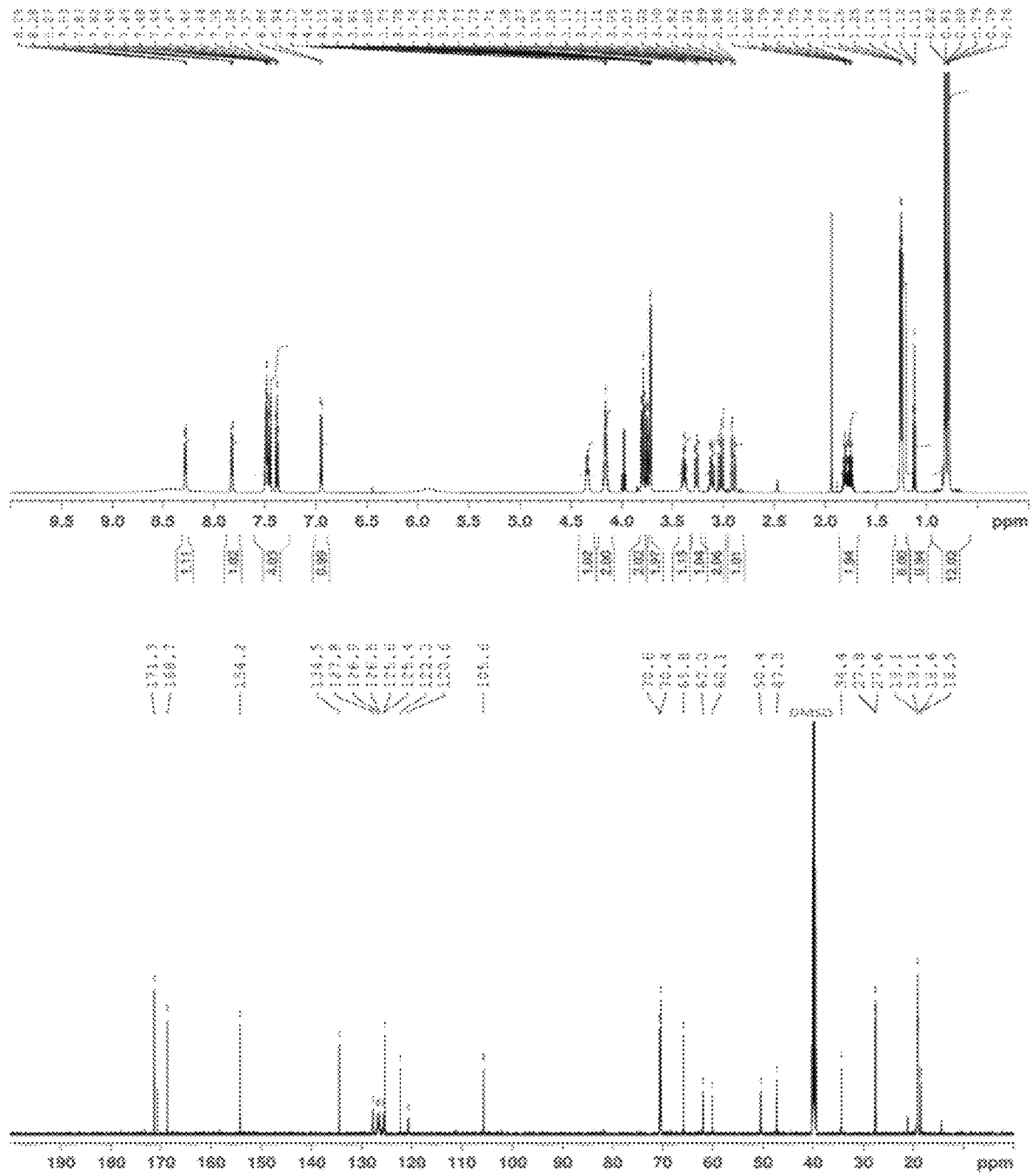
FIG. 2 is an NMR spectra of synthesized PRL:C4 melt or ionic liquid.
Figure 3:
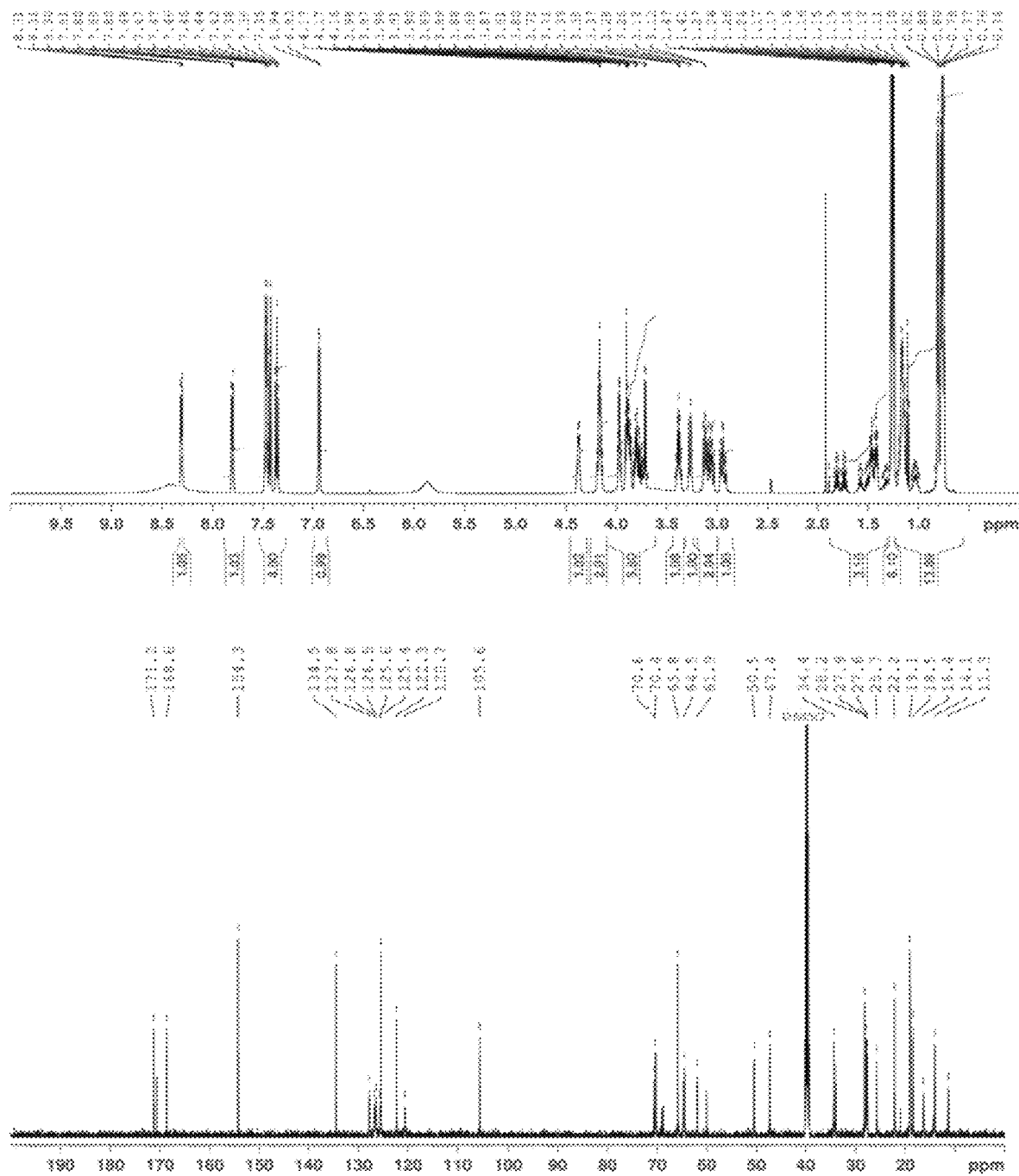
FIG. 3 is an NMR spectra of synthesized PRL:C5 melt or ionic liquid.

Preparation of Propranolol Melts or Ionic Liquids:

Preparation of Propranolol-Diisobutyl Sulfosuccinate (PRL:C4):

Sodium diisobutyl sulfosuccinate (Pfaltz & Bauer, Waterbury, Conn.; 4.08 g, 0.012 mol) was added to a solution of propranolol hydrochloride (3.63 g, 0.012 mol) in 100 mL ddH$_2$O. The mixture was stirred for 15 minutes at atmospheric pressure, and 80 mL of chloroform was added, followed by 1 hour of stirring at atmospheric pressure. Water was removed using a separation funnel, and chloroform was washed in the separation funnel with 3×100 mL of ddH$_2$O, until a test of the water with Quantofix chloride test strips showed no presence of chloride. Chloroform was removed by rotary evaporation, and the resulting propranolol melt or ionic liquid was dried in a vacuum oven at 60° C. for 36 hours. The propranolol melt or ionic liquid was stored in a desiccator with silica gel until use. $^1$H and $^{13}$C NMR assignments for PRL:C4 are provided as follows: $^1$H NMR (DMSO-d6) δ 8.28 (m, 1H), 7.83 (m, 1H), 7.45 (m, 4H), 6.95 (d, J=7.6 Hz, 1H), 4.34 (m, 1H), 4.16 (sep, J=4.7 Hz, 2H), 3.80 (m, 2H), 3.73 (m, 2H), 3.38 (sep, J=6.5 Hz, 1H), 3.26 (dd, J=2.9, 2.8 Hz, 1H), 3.08 (m, 2H), 2.90 (dd, J=3.6, 3.6 Hz, 1H), 1.78 (m, 2H), 1.25 (dd, J=6.6, 6.6 Hz, 6H), 1.12 (t, J=7.1 Hz, 1H), 0.80 (m, 12H). $^{13}$C NMR (DMSO-d6) δ 171.3, 168.7, 154.2, 134.5, 127.8, 126.9, 126.5, 125.6, 125.4, 122.3, 120.6, 105.6, 70.6, 70.4, 65.8, 62.0, 60.1, 50.4, 47.3, 34.4, 27.8, 27.6, 19.1, 19.1, 19.1, 19.1, 18.6, 18.5. Spectra are also provided (FIG. 2).

Figure 4:
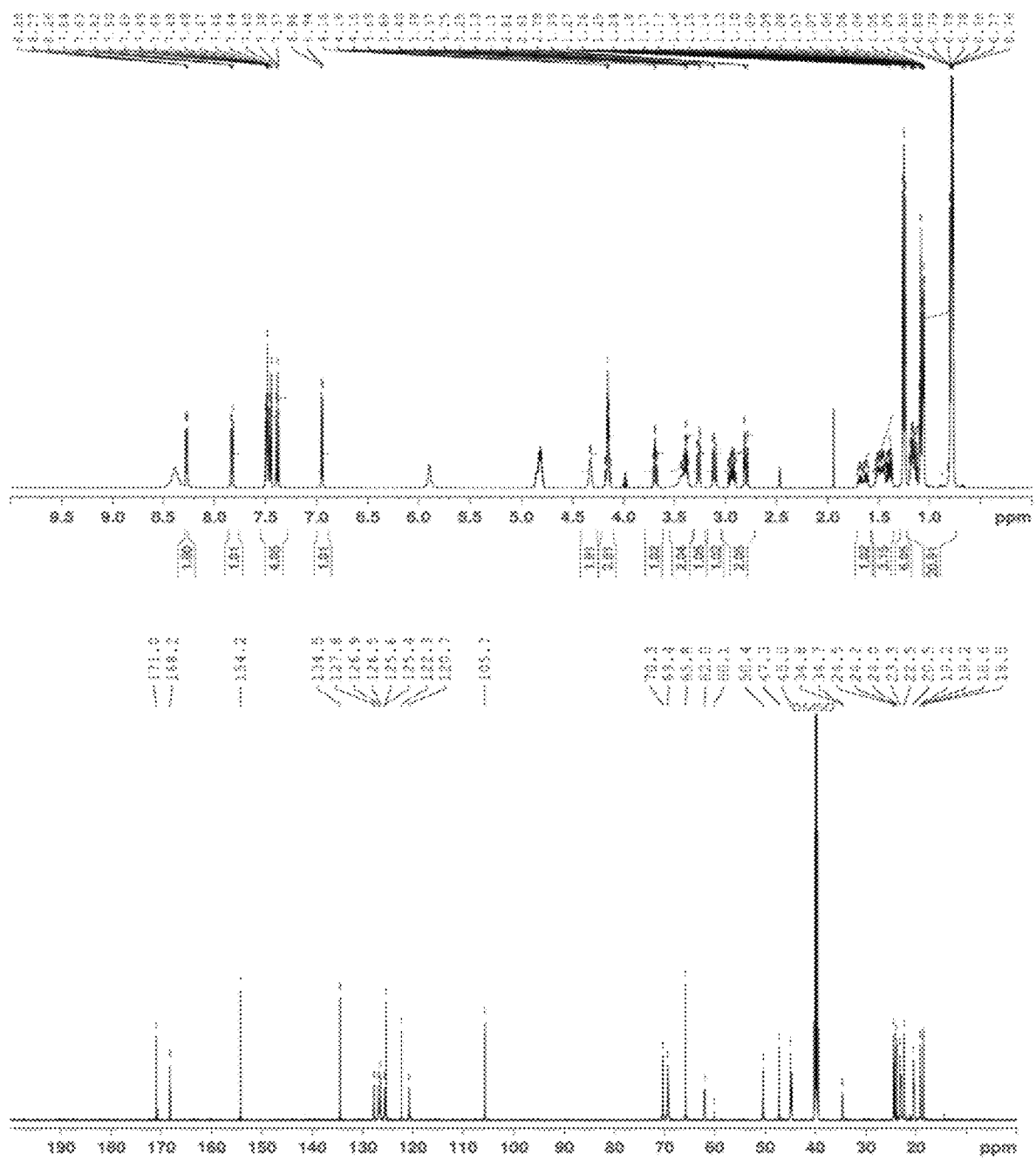
FIG. 4 is an NMR spectra of synthesized PRL:C6 melt or ionic liquid.

Preparation of Propranolol-Dihexyl Sulfosuccinate (PRL:C6):

Sodium dihexyl sulfosuccinate solution (Sigma-Aldrich, St. Louis, Mo.; 80% in H2O, 7.79 g, 0.016 mol) was added to a solution of propranolol hydrochloride (4.75 g, 0.016 mol) in 150 mL ddH2O. The mixture was stirred for 15 minutes at atmospheric pressure, and 100 mL of chloroform was added, followed by 1 hour of stirring at atmospheric pressure. The resulting propranolol melt was subsequently processed and stored as described above. $^1$H and $^{13}$C NMR assignments for PRL:C6 are provided as follows: $^1$H NMR (DMSO-d6) δ 8.27 (m, 1H), 7.83 (m, 1H), 7.46 (m, 4H), 6.95 (d, J=7.4 Hz, 1H), 4.32 (m, 1H), 4.16 (sep, J=5.0 Hz, 2H), 3.69 (m, 1H), 3.40 (m, 2H), 3.26 (dd, J=2.8, 2.7 Hz, 1H), 3.11 (dd, J=9.6, 9.6 Hz, 1H), 2.86 (m, 2H), 1.65 (m, 1H), 1.45 (m, 3H), 1.25 (dd, J=6.6, 6.6 Hz, 6H), 0.81 (m, 21H). $^{13}$C NMR (DMSO-d6) δ 171.0, 168.2, 154.2, 134.5, 127.8, 126.9, 126.5, 125.6, 125.4, 122.3, 120.7, 105.7, 70.3, 69.4, 65.8, 62.0, 60.1, 50.4, 47.3, 45.0, 34.8, 34.7, 24.5, 24.2, 24.0, 23.3, 22.5, 20.5, 19.2, 19.2, 18.6, 18.5. Spectra are also provided (FIG. 4).

Figure 5:
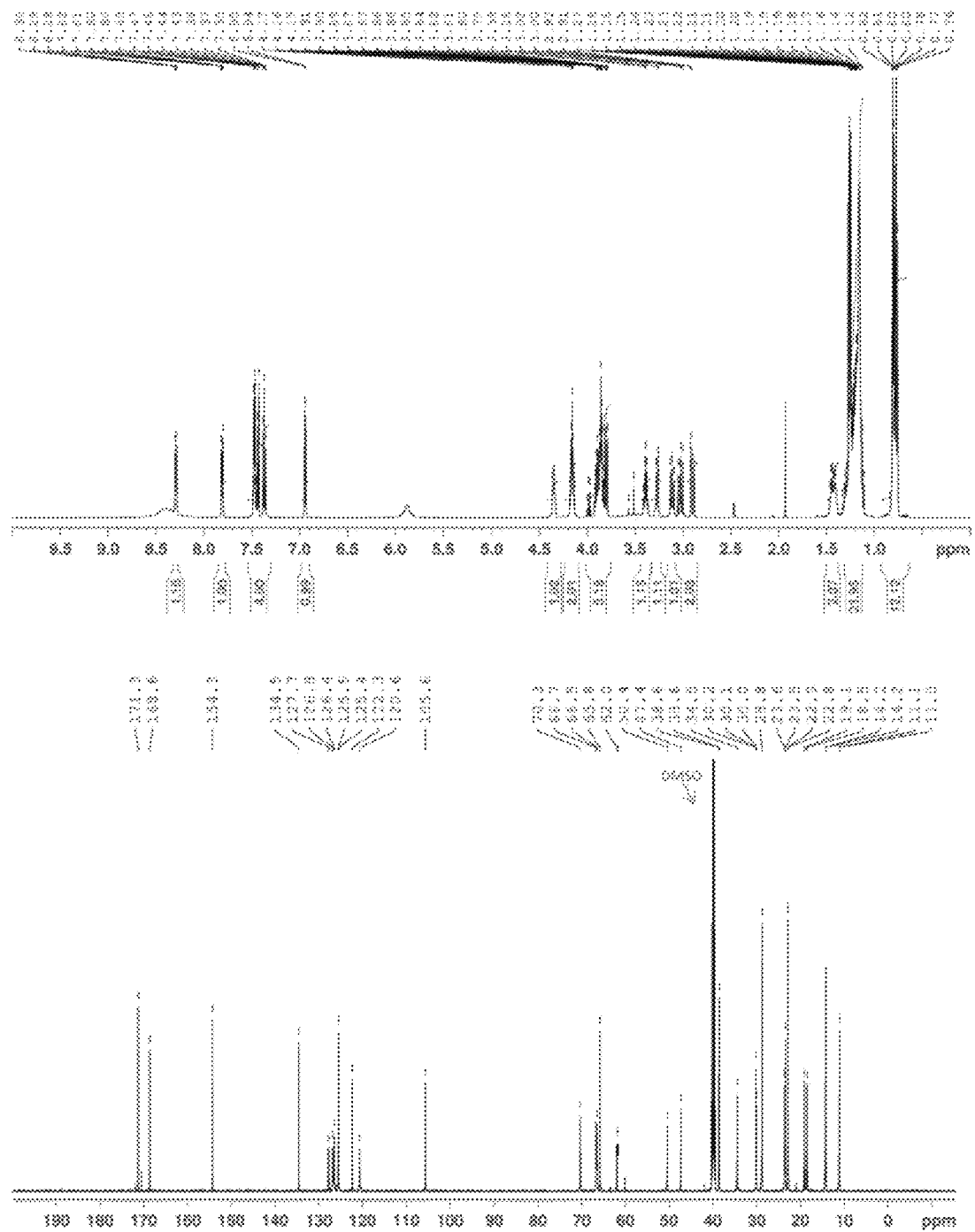
FIG. 5 is an NMR spectra of synthesized PRL:C8.

Preparation of Propranolol-Dioctyl Sulfosuccinate (PRL:C8):

Sodium dioctyl sulfosuccinate (Sigma-Aldrich, St. Louis, Mo.; 6.35 g, 0.014 mol) was added to a solution of propranolol hydrochloride (4.23 g, 0.014 mol) in 100 mL ddH2O. The mixture was stirred for 15 minutes at atmospheric pressure, and 100 mL of chloroform was added, followed by 30 minutes of stirring at atmospheric pressure. The resulting propranolol melt or ionic liquid was subsequently processed and stored as described above. $^1$H and $^{13}$C NMR assignments for PRL:C8 are provided as follows: $^1$H NMR (DMSO-d6) δ 8.29 (m, 1H), 7.81 (m, 1H), 7.43 (m, 4H), 6.95 (d, J=7.6 Hz, 1H), 4.35 (m, 1H), 4.16 (sep, J=5.8 Hz, 2H), 3.86 (m, 5H), 3.39 (sep, J=6.5 Hz, 1H), 3.27 (dd, J=2.7, 2.6 Hz, 1H), 3.11 (dd, J=9.6, 9.6 Hz, 1H), 2.97 (m, 2H), 1.43 (m, 2H), 1.26 (dd, J=6.6, 6.6 Hz, 6H), 1.16 (m, 16H), 0.79 (m, 12H). $^{13}$C NMR (DMSO-d6) δ 171.3, 168.6, 154.3, 134.5, 127.7, 126.8, 126.4, 125.5, 125.4, 122.3, 120.6, 105.6, 70.3, 66.7, 66.5, 65.8, 62.0, 50.4, 47.4, 38.6, 38.6, 34.5, 30.2, 30.1, 30.0, 28.8, 23.6, 23.5, 22.9, 22.8, 19.1, 18.5, 14.2, 14.2, 11.1, 11.0. Spectra are also provided (FIG. 5).

Density and Conductivity:

Density was measured one time per propranolol melt or ionic liquid using a 1-mL volumetric flask and an analytical balance. Conductivity of neat melts or ionic liquids, melts in water, and melts in octanol was measured on a benchtop conductivity meter DS-71 (Horiba, Kyoto, Japan) with a flow type conductivity electrode 3574-10C (Horiba, Kyoto, Japan) and calibrated with KCl standard solutions. Conductivity was measured three times per sample using 0.25-mL samples at 25° C. and 37° C., and divided by molarity of solute.

Preparation of 3H-Labeled Propranolol Melts or Ionic Liquids:

3H-labeled PFB in ethanol solution was obtained from Perkin Elmer (Waltham, Mass.). The 3H-labeled free base solution was directly added to propranolol melts or ionic liquids at a concentration of 10 µCi/mL. The mixture was stirred with a spatula, and allowed to equilibrate for 48 hours, followed by confirmation of uniformity of radiolabeled solute by measuring concentration using a scintillation counter (Packard Tri-Carb 2100 TR, Meriden, Conn.).

Determination of Partition Coefficient in n-Octanol/Water:

A 250 mL volume of n-octanol was shaken with 25 mL of ddH$_2$O and left overnight to obtain n-octanol saturated with water. A 250 mL volume of ddH$_2$O was shaken with 25 mL of n-octanol and left overnight to obtain water saturated with n-octanol. Ten milliliters of saturated n-octanol was added to each 3H-labeled propranolol melt or ionic liquid (6-10 mg) in a 20-mL scintillation vial followed by stirring until the melt or ionic liquid was dissolved completely. 10 mL saturated water was shaken with 10 mL of the 3H-labeled propranolol melt or ionic liquid solution in octanol for 1 minute, followed by 2 minutes of gentle centrifugation (1000 rpm, 74×g, Allegra X-12R centrifuge, FX6100 rotor, Beckman Coulter, Brea, Calif.) to obtain clean separation of the two layers. Ten milliliters of Ultima Gold (Perkin Elmer, Waltham, Mass.) was shaken with a 1-mL portion of the octanol layer or water layer in a 20-mL scintillation vial. The concentration of radiolabeled propranolol in the octanol layer and water layer was measured using a scintillation counter and standard solution of radiolabeled propranolol melts or ionic liquid. The partition coefficient n-octanol/water was calculated as the logarithm of the concentration of propranolol in octanol divided by the concentration of propranolol in water.

Measurement of Skin Transport:

Franz diffusion cells were used to assess the skin transport of propranolol melts or ionic liquids using a previously established protocol described in Karande, P., et al., Discovery of transdermal penetration enhancers by high-throughput screening. Nat. Biotechnol. 22, 192-197 (2004). Briefly, the acceptor chamber was filled with degas sed PBS or 4% bovine serum albumin in PBS and a small stir bar was added. Thawed porcine skin was clamped in place between the acceptor and donor chambers with the SC facing up. Care was taken to ensure no air bubbles resided in the acceptor chamber, and skin was stretched to minimize the presence of furrows. PFB solution in either IPM or EtOH was spiked with the 3H-labeled propranolol free base solution to a final concentration of 10 µCi/mL. Alternatively, 3H-labeled propranolol melts or ionic liquids were used as donor formulations. Donor solution (300 µL) was added enough to cover the whole donor chamber (1.77 cm2) and incubated in contact with the SC for 24 hours, at 37° C., with stirring. After 24 hours, the donor solution was removed, and the skin was thoroughly washed and dried. The SC was separated from epidermis by tape stripping. Ten tape strips were performed in an identical fashion, with each tape corresponding to one SC "layer". Ten strips were assumed to remove the majority of the SC. Epidermis was separated from dermis with a surgical scalpel, and the acceptor solution was collected from the acceptor chamber. Samples from each tissue layer and acceptor solution were dissolved in Solvable (Perkin Elmer, Waltham, Mass.) overnight, and the amount of propranolol was measured using a scintillation counter and standard solution of radiolabeled donors. In addition, concentration of propranolol in whole SC, epidermis, dermis and acceptor was estimated assuming that thickness of whole SC, epidermis and dermis were 26, 66 and 3,338 µm, respectively, as described in Bronaugh, R. L., et al., Methods for in vitro percutaneous absorption studies II. Animal models for human skin. Toxicol. Appl. Pharmacol. 62, 481-488 (1982). Furthermore, permeability ($K_p$) was calculated using the following equation, where $J_{ss}$ is the steady-state flux calculated as the slope of the linear portion of the plot of the cumulative amount permeated per unit area versus time, and C is propranolol concentration in donor. This calculation assumed that steady state was achieved within 24 hours with minimal lag time:

$$K_p(\text{cm/hr}) = \frac{J_{ss}(\text{mg}\cdot\text{cm}^{-2}\cdot\text{hr}^{-1})}{C(\text{mg}\cdot\text{cm}^{-3})}.$$

Measurement of Skin Irritation:

Skin irritation was assessed by measuring interleukin-1α release from Mat Tek Epiderm FT™ human skin equivalent tissues (MatTek Corporation, Ashland, Mass.). Experiments were performed according to the manufacturer's recommended protocol. Briefly, new media was added immediately before application of formulations. Formulations were applied to the surface of the tissues for 4 hours. After 4 hours, 200 µL of media was collected for interleukin-la analysis. Interleukin-la release was quantified using a Human Interleukin-la ELISA Kit (Pierce Biotechnology Inc., Rockford, Ill.) according to the manufacturer's recommended Protocol. ThermoFisher Scientific. Instructions of Human IL-1α ELISA Kit. Retrieved from https://www.thermofisher.com/order/catalog/product/EH2IL1A (2014). Absorbance of blank (0 pg/mL Interleukin-1α) was subtracted from absorbance of each sample.

Statistics:

Data reported are mean±SD except where otherwise noted. Where appropriate, statistical significance was confirmed by one-way analysis of variance (ANOVA) followed by Bonferroni post-hoc test using Microsoft Excel. The level of significance was set at $p<0.05$.

NMR Spectroscopy:

NMR spectroscopy was performed to define identities of starting materials and final products. Proton NMR and carbon NMR ($^1$H and $^{13}$C NMR) datasets were collected on a 600-MHz Varian instrument using sample concentrations of ~50 mM in DMSO-d6 or D2O. 1H spectra were averaged over 256 scans with a 2-second relaxation delay between pulses. $^{13}$C spectra were averaged over 1,000 scans with a 2-second relaxation delay between pulses. Assignments for each starting material are provided below. Assignments for the propranolol free base (PFB) and each propranolol melt are provided in the corresponding synthesis section.

NMR Assignments of Starting Materials:

NMR assignments for C4 are provided as follows: $^1$H NMR (DMSO-$d_6$) δ 3.70 (m, 4H), 3.11 (d, J=6.4 Hz, 1H), 2.91 (dd, J=11.6, 11.8 Hz, 1H), 2.80 (dd, J=3.7, 3.4 Hz, 1H), 1.65 (m, 2H), 0.79 (m, 13H). $^{13}$C NMR (DMSO-$d_6$) δ 171.4, 168.7, 70.6, 68.2, 61.8, 34.2, 30.7, 27.6, 19.2, 19.2, 19.1, 19.1. NMR assignments for C5 are provided as follows: $^1$H NMR (DMSO-$d_6$) δ 3.85 (m, 6H), 2.85 (m, 2H), 1.22 (m, 17H). 13C NMR (DMSO-d6) δ 171.4, 168.9, 68.8, 64.5, 61.8, 34.1, 28.2, 27.9, 27.8, 25.7, 22.2, 16.5, 14.2, 11.4.

NMR Assignments for C6 are Provided as Follows:

$^1$H NMR (DMSO-$d_6$) δ 3.64 (m, 1H), 3.40 (m, 1H), 2.80 (m, 2H), 1.52 (m, 4H), 1.01 (m, 21H). $^{13}$C NMR (DMSO-$d_6$) δ 170.0, 168.4, 69.4, 61.9, 56.5, 44.9, 34.5, 34.4, 24.5, 24.2, 24.0, 23.2, 22.4, 20.5, 18.8, 18.8. Spectra are also provided (FIG. 4). NMR assignments for C8 are provided as follows: 1H NMR (DMSO-d6) δ 3.86 (m, 4H), 3.70 (dd, J=3.5, 3.5 Hz, 1H), 2.92 (dd, J=11.7, 11.7 Hz, 1H), 2.81 (dd, J=3.4, 3.4 Hz, 1H), 1.46 (quin, J=5.9 Hz, 2H), 1.26 (m, 16H), 0.80 (m, 12H). $^{13}$C NMR (DMSO-$d_6$) δ 171.4, 168.9, 66.7, 66.5, 61.8, 38.6, 38.6, 34.3, 30.2, 30.1, 30.0, 28.8, 23.6, 23.4, 22.8, 22.8, 14.4, 14.2, 11.1, 11.1.

NMR Assignments for PRL:Cl are Provided as Follows:

$^1$H NMR (D$_2$O) δ 7.98 (m, 1H), 7.46 (m, 1H), 7.21 (m, 4H), 6.55 (d, J=7.3 Hz, 1H), 4.12 (m, 1H), 3.82 (m, 2H), 3.07 (sep, J=6.7 Hz, 1H), 2.85 (m, 2H), 1.07 (dd, J=6.6, 6.6 Hz, 6H). $^{13}$C NMR (D$_2$O) δ 153.4, 134.0, 127.5, 126.6, 126.2, 125.6, 124.8, 121.4, 120.7, 105.6, 69.4, 65.5, 50.9, 46.6, 18.2, 18.2.

Preparation of Propranolol Free Base:

One molar equivalent of sodium hydroxide aqueous solution was added to an aqueous solution of propranolol hydrochloride (Fisher Scientific, Pittsburgh, Pa.). The mixture was stirred for 15 minutes followed by extraction in ethyl acetate, and was subsequently washed with water, until a water test with Quantofix chloride strips (Macherey-Nagel, Bethlehem, Pa.) showed no presence of chloride. Evaporation of the ethyl acetate yielded propranolol free base, which was stored at −20° C. until use. $^1$H and $^{13}$C NMR assignments for PFB are provided as follows: $^1$H NMR (DMSO-$d_6$) δ 8.24 (m, 1H), 7.81 (m, 1H), 7.43 (m, 4H), 6.91 (d, J=7.4 Hz, 1H), 4.08 (m, 3H), 2.70 (m, 3H), 0.97 (dd, J=2.4, 2.3 Hz, 6H). $^{13}$C NMR (DMSO-d6) δ 154.7, 134.5, 127.8, 126.8, 126.7, 126.6, 125.5, 122.2, 120.3, 105.6, 71.5, 69.0, 50.6, 48.7, 23.4, 23.4. Spectra are also provided (FIG. 1).

CHN Elemental Analysis:

CHN elemental analysis was performed with a CE-440 Rapid Analysis Elemental Analyzer (Exeter Analytical, North Chelmsford, Mass.). Sample size was 1-3 mg weighed in small aluminum capsules. Capsules were placed in protective nickel sleeves, loaded into the autosampler wheel and introduced into the combustion furnace by means of a mechanically operated quartz ladle. Percent weights of carbon, nitrogen and hydrogen were determined by high-temperature combustion at 1,000° C. in an oxygen-enriched helium atmosphere.

Attenuated Total Reflection Fourier Transform Infrared Spectroscopy:

Attenuated total reflection Fourier transform infrared spectroscopy (ATR-FTIR) was performed using a Nicolet iS™ 10 spectrometer with a diamond crystal (Thermo Fisher, Waltham, Mass.). Spectra were collected with 2 cm$^{-1}$ resolution averaged over 100 scans. Propranolol melts were added drop wise to the crystal until the entire surface area of the crystal was covered. All melts were applied neat. Due to the hygroscopic nature of C6, it was applied as a concentrated water solution. All other samples were applied as a powder and pressed firmly onto the crystal to create a uniformly packed film.

Thermogravimetric Analysis:

Thermogravimetric analysis (TGA) was performed with a Thermo Gravimetric Analyzer/sDTA851c (Mettler Toledo, Columbus, Ohio). Sample size was 3-9 mg, and was weighed in an aluminum oxide crucible. Samples were heated from 25° C. to 1,000° C. under $N_2$ atmosphere with a ramp rate of 10° C. per minute.

Karl-Fischer Titration:

Water content was determined using the HYDRANAL® Moisture Test Kit (Sigma Aldrich, St. Louis, Mo.). Twenty milliliters of HYDRANAL Solvent E was added to the titration vessel. The solution in the vessel was constantly stirred. HYDRANAL Titrant Component was added drop wise until the solution in the vessel turned yellow in color. Then propranolol melt was added to the vessel and allowed to dissolve completely. The sample solution was then titrated again with HYDRANAL Titrant Component under constant mixing until a color change from colorless to yellow was again observed. Percent weight water content was calculated as follows:

$$\text{Concentration (\% Weight)} = \frac{\text{Titrant (mL)} \times 5 \text{ mg}\frac{H_2O}{mL} \times 100}{IL \text{ Volume } (\mu L) \times IL \text{ Density}\left(\frac{g}{mL}\right)}.$$

Silver Nitrate Precipitation:

One part weight of propranolol melt or ionic liquid was washed with two parts weight ddH$_2$O and two parts weight chloroform for 30 minutes. The aqueous phase was collected using a separation funnel. A concentrated solution of silver nitrate (Sigma Aldrich, St. Louis, Mo.) in ddH$_2$O (2 g/mL) was added drop wise to the aqueous phase and analyzed visually for the formation of precipitate Viscosity and Differential Scanning Calorimetry:

Viscosity was measured using 1-mL samples with a LC-ARES Test Station (TA Instruments, New Castle, Del.) and a cone (diameter: 25 mm; angle: 0.1 rad). The cone rotation rate was 10 s$^{-1}$ and viscosity was measured three times per sample at 25° C. and 37° C. Differential scanning calorimetry (DSC) was performed with a Q2000 DSC with 50 position autosampler (TA Instruments, New Castle, Del.). Sample size was 9-10 mg, and was weighed in an aluminum hermetic pan. Samples were heated from room temperature to 120° C. under $N_2$ atmosphere followed by cooling to ~150° C. and subsequent heating back to 120° C. with a ramp rate of 10° C. per minute.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A topical drug delivery formulation comprising a melt or ionic liquid of amorphous propranolol, wherein the formulation is in a form suitable for transdermal delivery, and wherein the form is selected from the group consisting of liquids, pastes, ointments, creams, gels, foams, and lotions.

2. The topical drug delivery formulation of claim 1, wherein the form is a liquid.

3. The topical drug delivery formulation of claim 1, wherein the formulation is in a patch.

4. The topical drug delivery formulation of claim 1, wherein the formulation contains a sufficient amount of amorphous propranolol to deliver a therapeutically effective amount of propranolol for the treatment or amelioration of infantile hemangioma.

5. The topical drug delivery formulation of claim 4, wherein the therapeutically effective amount of propranolol is in the range of about 0.1 to about 10 mg.

6. The topical drug delivery formulation of claim 1, wherein the melt or ionic liquid of propranolol comprises propranolol and a dialkyl sulfosuccinate.

7. The topical drug delivery formulation of claim 1, wherein the melt or ionic liquid of amorphous propranolol is an ionic liquid that is a liquid at room temperature.

8. The topical drug delivery formulation of claim 1, wherein the amorphous propranolol displays a higher flux rate compared to crystalline propranolol free base in a liquid formulation.

9. The topical drug delivery formulation of claim 8, wherein the crystalline propranolol free base in a liquid formulation is propranolol free base dissolved in ethanol.

10. The topical drug delivery formulation of claim 1, wherein the formulation further comprises one or more inactive ingredients.

11. The topical drug delivery formulation of claim 10, wherein the one or more inactive ingredients are selected from the group consisting of acrylates and polymers thereof, methacrylates and polymers thereof, cellulose polymers, hydroxyethyl cellulose and polymers thereof, hydroxypropyl cellulose and polymers thereof, poly-lactylate polymers, polyvinyl pyrrolidone polymers, ethylenevinylacetate copolymers, short, medium, and long chain fatty acid molecules and analogs thereof, isopropyl myristate, polyethylene terephthalate, polyethylene glycol and polymers thereof, vitamin C, vitamin C analogs or esters, vitamin E, vitamin E analogs, vitamin E polymeric compounds, d-α-tocopheryl polyethylene glycol 1000 succinate, silicone, and combinations thereof.

12. A topical drug delivery formulation comprising a melt or ionic liquid of amorphous propranolol, wherein the melt or ionic liquid is formed by a salt metathesis reaction.

13. The topical drug delivery formulation of claim 12, wherein the salt metathesis reaction comprises reacting propranolol hydrochloride with a sodium dialkyl sulfosuccinate.

14. The topical drug delivery formulation of claim 13, wherein the sodium dialkyl sulfosuccinate is sodium diisobutyl sulfosuccinate, sodium diamyl sulfosuccinate, sodium dihexyl sulfosuccinate, or sodium dioctyl sulfosuccinate.

15. A topical drug delivery formulation comprising a melt or ionic liquid of amorphous propranolol, wherein the melt or ionic liquid of amorphous propranolol is an ionic liquid that is a liquid at room temperature, wherein the melt or ionic liquid of amorphous propranolol has a low viscosity, and wherein the formulation does not contain an organic solvent.

16. The topical drug delivery formulation of claim 15, wherein the amorphous propranolol displays a higher flux rate compared to crystalline propranolol free base in a liquid formulation.

17. The topical drug delivery formulation of claim 16, wherein the crystalline propranolol free base in a liquid formulation is propranolol free base dissolved in ethanol.

18. The topical drug delivery formulation of claim 15, wherein the formulation further comprises one or more inactive ingredients.

19. The topical drug delivery formulation of claim 18, wherein the one or more inactive ingredients are selected from the group consisting of acrylates and polymers thereof, methacrylates and polymers thereof, cellulose polymers, hydroxyethyl cellulose and polymers thereof, hydroxypropyl cellulose and polymers thereof, poly-lactylate polymers, polyvinyl pyrrolidone polymers, ethylenevinylacetate copolymers, short, medium, and long chain fatty acid molecules and analogs thereof, isopropyl myristate, polyethylene terephthalate, polyethylene glycol and polymers thereof, vitamin C, vitamin C analogs or esters, vitamin E, vitamin E analogs, vitamin E polymeric compounds, d-α-tocopheryl polyethylene glycol 1000 succinate, silicone, and combinations thereof.

20. A composition comprising a compound of formula (I)

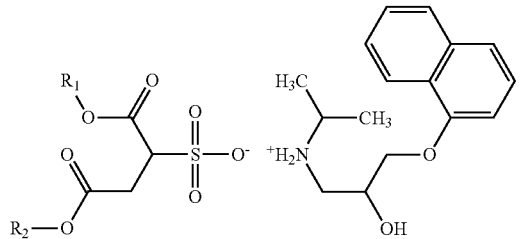

Formula I wherein each of $R_1$ and $R_2$ is independently a $C_3$-$C_{14}$ alkyl chain, wherein the composition is free of aqueous and organic solvents.

21. The composition of claim 20, wherein the compound is an amorphous melt or ionic liquid.

22. The composition of claim 20, wherein the compound is formed by a salt metathesis reaction.

23. The composition of claim 22, wherein the salt metathesis reaction comprises reacting propranolol hydrochloride with a sodium dialkyl sulfosuccinate selected from the group consisting of sodium diisobutyl sulfosuccinate, sodium diamyl sulfosuccinate, sodium dihexyl sulfosuccinate, and sodium dioctyl sulfosuccinate.

24. A composition comprising a melt or ionic liquid of an amorphous compound of formula (I)

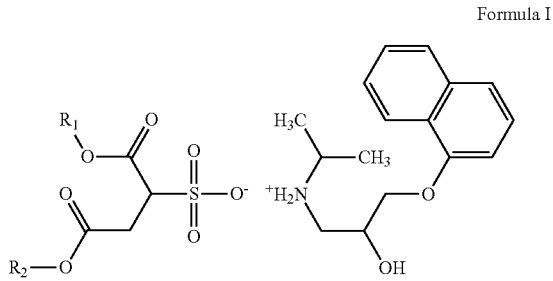

Formula I wherein each of $R_1$ and $R_2$ is independently a $C_3$-$C_{14}$ alkyl chain, in a topical drug delivery formulation.

25. The composition of claim 24, wherein the topical drug delivery formulation is in a form suitable for transdermal administration.

26. The composition of claim 25, wherein the form is selected from the group consisting of liquids, pastes, ointments, creams, gels, foams, and lotions.

27. The composition of claim 24, wherein the formulation contains a sufficient amount of the amorphous compound to deliver a therapeutically effective amount of propranolol for the treatment or amelioration of infantile hemangioma.

28. The composition of claim 27, wherein the therapeutically effective amount of propranolol is in the range of about 0.1 to about 10 mg.

* * * * *